(12) United States Patent
Schiemanck et al.

(10) Patent No.: US 10,561,425 B2
(45) Date of Patent: Feb. 18, 2020

(54) SYSTEM AND METHOD FOR TREATING HEART TISSUE

(71) Applicant: Miracor Medical SA, Awans (BE)

(72) Inventors: Lars Roman Schiemanck, Baden (AT); Martin Haidacher, Rauris (AT)

(73) Assignee: Miracor Medical SA, Vienna (AT)

( * ) Notice: Subject to any disclaimer, the term of this patent is extended or adjusted under 35 U.S.C. 154(b) by 183 days.

(21) Appl. No.: 15/858,856

(22) Filed: Dec. 29, 2017

(65) Prior Publication Data
US 2018/0221027 A1   Aug. 9, 2018

Related U.S. Application Data

(62) Division of application No. 14/102,958, filed on Dec. 11, 2013, now Pat. No. 9,855,049.

(51) Int. Cl.
*A61M 29/00*    (2006.01)
*A61F 2/958*    (2013.01)
(Continued)

(52) U.S. Cl.
CPC ........ *A61B 17/1204* (2013.01); *A61B 5/0215* (2013.01); *A61B 5/6853* (2013.01);
(Continued)

(58) Field of Classification Search
CPC .... A61M 29/00; A61M 25/10; A61M 25/104; A61F 2/958; A61B 17/1204; A61B 17/12; A61B 17/12122; A61B 17/12136
See application file for complete search history.

(56) References Cited

U.S. PATENT DOCUMENTS 4,459,977 A  *  7/1984  Pizon ................. A61M 1/3621
                                                        600/16
4,493,697 A      1/1985  Krause et al.
(Continued)

FOREIGN PATENT DOCUMENTS

DE    19514638    10/1996
DE    19526784     1/1997
(Continued)

OTHER PUBLICATIONS

'Cannulation' [online]. Medtronic, Inc. 2010 [retrieved May 27, 2010]. Retrieved from the Internet: <URL: http://www.medtronic.com/for-healthcare-professionals/products-therapies/cardiovascular/therapies/cannulation/index.htm>, 1 pp.
(Continued)

*Primary Examiner* — Vi X Nguyen
(74) *Attorney, Agent, or Firm* — Fish & Richardson P.C.

(57) ABSTRACT

Some embodiments of a system or method for treating heart tissue can include a control system and catheter device operated in a manner to intermittently occlude a heart vessel for controlled periods of time that provide redistribution of blood flow. In particular embodiments, the system can be configured to provide an estimation of the cumulative effects of the treatment. For example, some embodiments of the system or method can treat myocardium that is at risk of infarction by intermittently altering blood flow in a venous system to induce microcirculation within the myocardium, and can output a cumulative dosage value indicative of a measurement of progress of reducing an infarct size.

20 Claims, 11 Drawing Sheets

(51) Int. Cl.
*A61B 17/12* (2006.01)
*A61B 5/0215* (2006.01)
*A61B 5/00* (2006.01)
*A61B 17/00* (2006.01)
*A61B 5/042* (2006.01)

(52) U.S. Cl.
CPC .......... *A61B 5/6869* (2013.01); *A61B 17/12* (2013.01); *A61B 17/12109* (2013.01); *A61B 17/12122* (2013.01); *A61B 17/12136* (2013.01); *A61B 5/0422* (2013.01); *A61B 5/7239* (2013.01); *A61B 2017/00154* (2013.01); *A61B 2017/00199* (2013.01); *A61B 2017/00243* (2013.01); *A61B 2217/005* (2013.01); *A61B 2505/05* (2013.01)

(56) References Cited

U.S. PATENT DOCUMENTS

| | | | |
|---|---|---|---|
| 4,589,869 | A | 5/1986 | Wemborg |
| 4,657,536 | A | 4/1987 | Dorman |
| 4,671,796 | A | 6/1987 | Groshong et al. |
| 4,701,166 | A | 10/1987 | Groshong et al. |
| 4,705,501 | A | 11/1987 | Wigness et al. |
| 4,887,608 | A | 12/1989 | Mohl et al. |
| 4,934,996 | A | 6/1990 | Mohl et al. |
| 4,943,277 | A | 7/1990 | Bolling |
| 4,969,470 | A | 11/1990 | Mohl et al. |
| 5,011,468 | A | 4/1991 | Lundquist et al. |
| 5,024,668 | A | 6/1991 | Peters et al. |
| 5,033,998 | A | 7/1991 | Corday et al. |
| 5,156,600 | A | 10/1992 | Young |
| 5,224,938 | A | 7/1993 | Fenton, Jr. |
| 5,226,427 | A | 7/1993 | Buckberg et al. |
| 5,466,216 | A | 11/1995 | Brown et al. |
| 5,707,358 | A | 1/1998 | Wright |
| 5,755,686 | A | 5/1998 | O'Neill et al. |
| 5,779,685 | A | 7/1998 | Thompson et al. |
| 6,458,323 | B1 | 10/2002 | Boekstegers |
| 6,500,145 | B1 | 12/2002 | Bicakci et al. |
| 6,506,146 | B1 | 1/2003 | Mohl et al. |
| 6,569,145 | B1 | 5/2003 | Shmulewitz et al. |
| 6,755,821 | B1 | 6/2004 | Fry |
| 7,083,588 | B1 | 8/2006 | Shmulewitz et al. |
| 7,331,922 | B2 | 2/2008 | Mohl |
| 8,162,813 | B2 | 4/2012 | Mohl |
| 8,177,704 | B1 * | 5/2012 | Mohl .................. A61B 5/6859 600/16 |
| 8,500,623 | B2 | 8/2013 | Mohl |
| 2002/0091349 | A1 | 7/2002 | Reich |
| 2002/0120232 | A1 | 8/2002 | Stumpp et al. |
| 2003/0100911 | A1 | 5/2003 | Nash et al. |
| 2004/0098030 | A1 | 5/2004 | Makower et al. |
| 2004/0220522 | A1 | 11/2004 | Briscoe et al. |
| 2005/0059930 | A1 | 3/2005 | Garrison et al. |
| 2005/0113799 | A1 | 5/2005 | Lenker |
| 2006/0100550 | A1 | 5/2006 | Schultheiss et al. |
| 2006/0173298 | A1 | 8/2006 | Tucker |
| 2006/0246044 | A1 | 11/2006 | Lutz et al. |
| 2006/0258980 | A1 | 11/2006 | Bridges et al. |
| 2007/0203445 | A1 | 8/2007 | Kaye et al. |
| 2008/0015404 | A1 | 1/2008 | Mohl |
| 2008/0119742 | A1 | 5/2008 | Mohl |
| 2010/0056849 | A1 | 3/2010 | Mohl |
| 2010/0130810 | A1 | 5/2010 | Mohl |
| 2011/0295302 | A1 | 12/2011 | Mohl |
| 2013/0165736 | A1 | 6/2013 | Mohl et al. |
| 2013/0317284 | A1 | 11/2013 | Mohl |

FOREIGN PATENT DOCUMENTS

| | | |
|---|---|---|
| EP | 0230996 | 8/1987 |
| EP | 1188417 | 3/2002 |
| UA | 14911 U | 6/2006 |
| WO | WO 1989/010155 | 11/1989 |
| WO | WO 2000/033913 | 6/2000 |
| WO | WO 2002/005887 | 1/2002 |
| WO | WO 2003/008018 | 1/2003 |

OTHER PUBLICATIONS

'Cardioplegia Delivery' [online]. Quest Medical, Inc. 2010 [retrieved May 27, 2010]. Retrieved from the Internet: <URL: http://www.questmedical.com/products/cardio_catheters.asp>, 3 pages.

'Global Myocardial Protection' [online]. Edwards Lifesciences, 2004 [retrieved May 27, 2010]. Retrieved from the Internet: <URL: http://ht.edwards.com/resourcegallery/products/cannulae/images/ar00519.pdf>, 1 page.

'Letters to the Editor: A New Technique for Pulmonary Arterial Catheter Insertion into Coronary Sinus Using Transesophageal Echocardiography' [online]. International Anesthesia Research Society, 2003 [retrieved May 27, 2010]. Retrieved from the Internet: <URL: http://www.anesthesia-analgesia.org/content/97/1/298.full.pdf>, 14 pages.

'MiRCSP Cannulae' [online]. Medtronic, Inc. 2010 [retrieved May 27, 2010]. Retrieved from the Internet: <URL: http://www.medtronic.com/for-healthcare-professionals/products-therapies/cardiovascular/cannulae-products/mircsp-cannula/index.htm>, 2 pp.

'Myocardial Protection System' [online]. Quest Medical, Inc. 2010 [retrieved May 27, 2010]. Retrieved from the Internet: <URL: http://www.questmedical.com/products/mps.asp>, 7 pp.

'Performer CPB' [online]. Medtronic, Inc. 2007 [retrieved May 27, 2010]. Retrieved from the Internet: <URL: http://www.medtronic.com/cardsurgery/arrested_heart/downloads/200704933.pdf>, 8 pp.

'Retrograde Perfusion Cannulae' [online]. Medtronic, Inc. 2010 [retrieved May 27, 2010]. Retrieved from the Internet: <URL: http://www.medtronic.com/for-healthcare-professionals/products-therapies/cardiovascular/cannulae-products/retrograde-perfusion-cannulae/index.htm>, 2 pp.

Alzubaidi et al., "Electrocardiogram based Methodology for Computing of Coronary Sinus Pressure." *International Journal of Computer Science Issues*, May 2011, 8(2):382-386.

Alzubaidi, "Accurate Methods of Calculating the Coronary Sinus Pressure Plateau." *International Journal of Computer Science Issues*, Jan. 2011, 8(1):138-140.

Faxon et al., "Coronary Sinus Occlusion Pressure and Its Relation to Intracardiac Pressure." *The American Journal of Cardiology*, Sep. 1985, 56:457-460.

Hoffman et al. "Usefulness of Myocardial Blush Grade Early and Late After Primary Coronary Angioplasty for Acute Myocardial Infraction in Predicting Left Ventricular Function." *The American Journal of Cardiology*, Nov. 2003, 92:1015-1019.

Lazar, "Advantages of Pressure-Controlled Intermittent Coronary Sinus Occlusion Over Left Ventricle-Powered Coronary Sinus Retroperfusion." *The Annals of Thoracic Surgery*, 2001, 71:402.

Mina et al., "Pressure Controlled Intermittent Coronary Sinus Occlusion (PICSO) in Patients Undergoing Cardiac Resynchronization Therapy." Biomedical Engineering, Austrian Research Centers, 2009, 1 pp.

Mohl et al., "Activation of Coronary Venous Endothelium as an Impulse for MyoCardial Regeneration." Academic Paper, Medical University of Vienna, 2006, 1 pp.

Mohl et al., "Analysis of Left Ventricular Function After Emergency Coronary Artery Bypass Grafting for Life-Threatening Ischaemia Following Primary Revascularisation." *European Journal of Cardio-thoracic Surgery*, 1998, 13:27-35.

Mohl et al., "Intermittent Pressure Elevation of the Coronary Venous System as a Method to Protect Ischemic Myocardium," *Interactive CardioVascular and Thoracic Surgery*, 2005, 4:66-69.

Mohl et al., "Is activation of coronary venous cells the key to cardiac regeneration?" Macmillan Publishers Ltd., *Nature Clinical Practice, Cardiovascular Medicine*, 2008, 5(9):528-530.

Mohl et al., "Myocardial Protection Via the Coronary Sinus Long-Term Effects of Intermittent Coronary Sinus Occlusion as an Adjunct to Reperfusion in Acute Myocardial Infarction." *Circulation Journal*, Apr. 2008, 72:526-533.

(56) References Cited

OTHER PUBLICATIONS

Mohl et al., "Reduction of Infarct Size Induced by Pressure-Controlled Intermittent Coronary Sinus Occlusion." *The American Journal of Cardiology*, Mar. 1984, 53:923-928.
Mohl et al., "The legacy of coronary sinus interventions: Endogenous cardioprotection and regeneration beyond stem cell research." The American Association for Thoracic Surgery, *The Journal of Thoracic and Cardiovascular Surgery*, 2008, 136(5):1131-1135.
Mohl, "Pressure Controlled Intermittent Coronary Sinus Occlusion—an Alternation to Retrograde Perfusion of Arterial Blood," *Society of Coronary Sinus Interventions*, 2002, 2-7.
Mohl, "The Momentum of Coronary Sinus Interventions Clinically." *Perspective*, Jan. 1988, 77(1):6-12.
Mohl et al. "Coronary Sinus Library, ICSO and PICSO," *Society of Coronary Sinus Interventions*, A. Holzhausens Nfg., Austria, 2003, 6 pp. (Table of Contents Only).
Onorati et al., "Continuous Coronary Sinus Perfusion Reverses Ongoing Myocardial Damage in Acute Ischemia," *Artificial Organs*, 2009, 33 (10):788-797.
Stone et al., "Impact of Normalized Myocardial Perfusion After Successful Angioplasty in Acute Myocardial Infarction," *Journal of the American College of Cardiology*, Feb. 2002, 39(4): 591-597.
Syeda et al., "The salvage potential of coronary sinus interventions: Meta-analysis and pathophysiologic consequences," *J Thorac Cardiovasc Surg.*, 2004, 124:1703-1712.
Weigel et al., "Beck and back: A paradigm change in coronary sinus interventions—pulsatile stretch on intact coronary venous endothelium," *The Journal of Thoracic and Cardiovascular Surgery*, Jun. 2007, 133(6):1581-1587.

\* cited by examiner

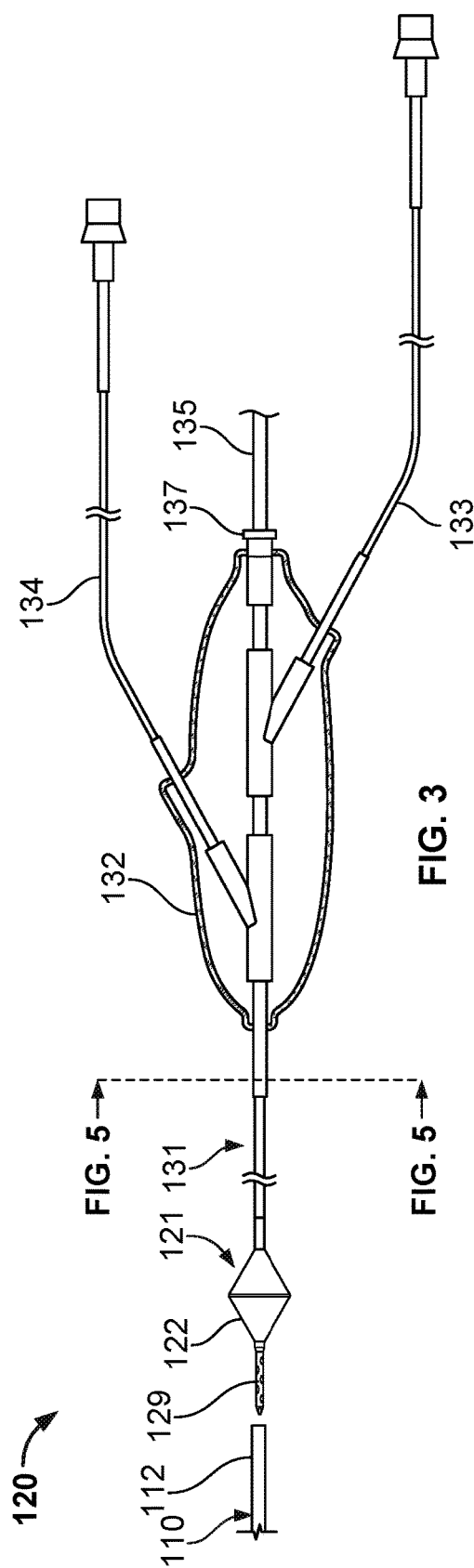
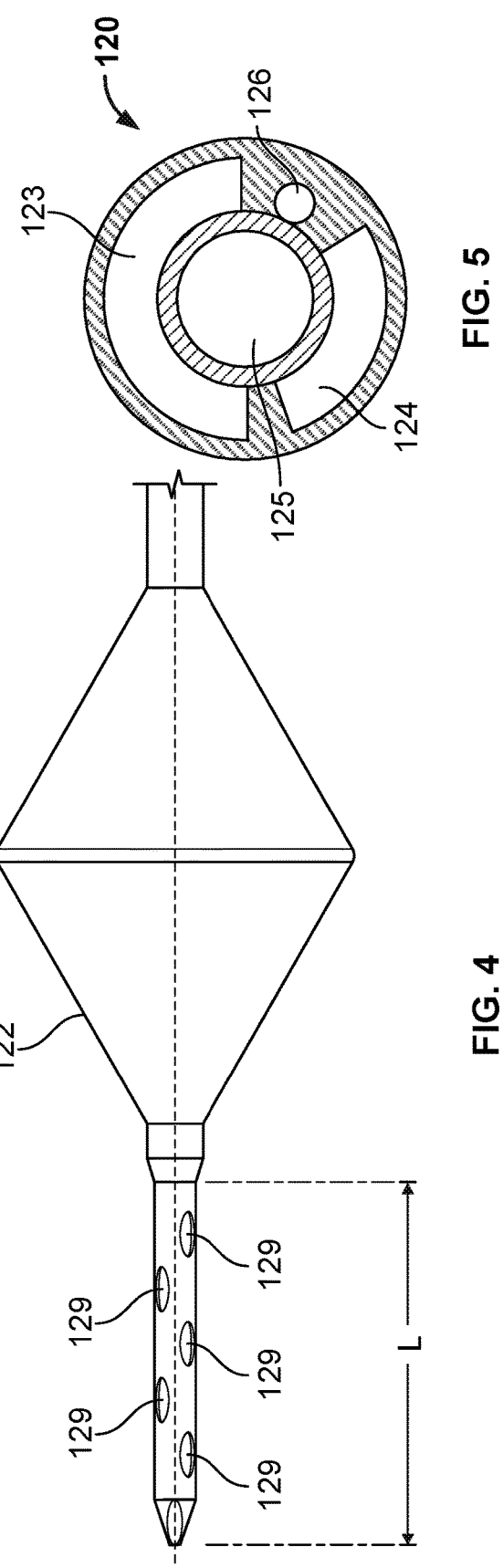
FIG. 3
FIG. 4
FIG. 5

SYSTEM AND METHOD FOR TREATING HEART TISSUE

TECHNICAL FIELD

This document relates to systems and methods for treating heart tissue, for example, by controlling an intermittent occlusion of venous blood flow in the heart.

BACKGROUND

The heart muscle receives arterial blood via coronary arteries so that the blood passes through and nourishes the heart muscle tissue. In some cases, a blockage in a coronary artery can result in a loss or reduction of blood flow through a portion of the heart muscle tissue, thereby creating an area at risk of ischemic death if the area is not timely reperfused. The injury of the ischemic heart muscle tissue may also be exacerbated by reperfusion injury from a sudden reperfusion of blood to tissue that had been deprived of adequate blood flow. After the blockage is removed or otherwise opened to resume blood flow, the ischemic portion of the heart muscle tissue (such as the reperfused microcirculation) may be damaged to the point that normal blood flow does not return through the ischemic portion of the muscle tissue.

Some conventional systems attempt to repair or treat the ischemic heart muscle tissue by supplying the ischemic tissue with blood through retrograde perfusion. For example, the coronary sinus may be temporarily occluded so that the blood therein counterflows back from the coronary sinus through the coronary venous system and toward the ischemic muscle tissue that previously did not receive blood from the arterial side. The occlusion of the coronary sinus causes a pressure increase and, as a result, a redistribution of venous blood via the respective vein(s) into the capillaries of the border-zone ischemic muscle tissue so as to improve the supply of nutrients to that ischemic area. When the occlusion is ceased so that blood exits normally through the coronary sinus, the venous blood is flushed out while the metabolic waste products from the damaged tissue are carried off at the same time.

The combination of repeated venous pressure build-up phases followed by a phase of redistribution of flow and wash-out, often referred to as an intermittent coronary sinus occlusion ("ICSO") method, might in some circumstances improve arterial blood demand, improve microcirculation by reducing microvascular obstructions, provide a cardioprotective effect, and reduce ischemic tissue infarct size. When the timing of the ICSO method (e.g., the occlusion times and the release times) is controlled based upon monitored pressure measurements, the method is often referred to as pressure-controlled ICSO, or "PISCO." A computer-implemented control system may be used to control the timing of when to start and when to end, and hence the duration of, the occlusion phases that are performed during a PICSO method.

SUMMARY

Some embodiments of a system or method for treating heart tissue can include a control system and a catheter device that are operated to intermittently occlude a heart vessel for controlled periods of time for purposes of redistributing blood flow, for example, toward a myocardial ischemic area or an area at risk (AAR) of ischemia. In particular embodiments, during the initiation of the treatment, the system can be configured to activate the catheter device and monitor patient characteristics to confirm that the system is attaining a satisfactory level of occlusion so as to provide a desired extent of blood redistribution. For example, in response to monitoring one or more patient characteristics after the catheter device is initially activated, the system can be configured to output an indication that the catheter position is satisfactory or that the catheter position should be adjusted. In some embodiments, during the treatment process, the system can be configured to determine and display a parameter representing a cumulative quantity of treatment provided over successive occlusion periods. In one example, the cumulative quantity that is calculated by the system can correlate to an estimated amount of AAR heart tissue that has been salvaged over the course of treatment provided, thereby providing practitioners with real-time feedback regarding the medical progress of the using the catheter device over the course of the successive occlusion periods. As such, the cumulative quantity or the estimated amount of AAR can be displayed and repeated updated by the control system over the course of the successive occlusion periods, which facilitates practitioner to more accurately determine whether to continue or end the treatment process using the catheter device.

Particular embodiments described herein may include a control system for a system for treating heart muscle tissue. The control system may include a sensor signal input to receive a pressure sensor data signal indicative of a pressure in the coronary sinus at least during two or more occlusion phases of a coronary sinus occlusion catheter (or another sensor data signal indicative of a bodily characteristic in the coronary sinus at least during two or more occlusion phases of a coronary sinus occlusion catheter). Also, the control system may include a control circuit including memory and a processor. The control circuit may be configured to determine, in response to stored data points of the pressure sensor data signal (or another bodily characteristic sensor data signal), a cumulative dosage value indicative of cumulative effects of coronary sinus occlusion catheter treatment over two or more successive occlusion phases.

In other embodiments, a computer-implemented method may include receiving a pressure sensor data signal indicative of a coronary sinus pressure after a occlusion catheter has substantially occluding the coronary sinus during an occlusion phase in a sequence of two or more occlusion phases. The method may also include calculating a cumulative dosage value indicative of cumulative effects of coronary sinus occlusion catheter treatment over the two or more successive occlusion phases.

In some embodiments, a control system for a system for treating heart muscle tissue may include a control system and a sensor signal input. The control system may be configured to selectively activate an occlusion device for substantially occluding the coronary sinus during occlusion phases, and configured to deactivate the occlusion device for substantially non-occluding the coronary sinus during release phases. The sensor signal input may be configured to receive a pressure sensor data signal indicative of a pressure in the coronary sinus at least during the occlusion phases. The control system may be configured to, in response to the pressure sensor data signal during at least one of the occlusion phases, output an alert indicating a recommendation to reposition of the occlusion device of the coronary sinus occlusion catheter.

In further embodiments described herein, a method may include receiving a pressure sensor data signal indicative of a coronary sinus pressure after a occlusion catheter has substantially occluded the coronary sinus during an occlusion phase of an occlusion device positioning test. The method may also include storing data indicative of at least pressure maxima and pressure minima measured during the sequence of multiple occlusion phases. The method may further include, after the occlusion phase of the occlusion device positioning test, calculating a pulsatile pressure parameter. The pulsatile pressure parameter may be calculated based at least in part upon the data the pressure maxima and pressure minima measured during the occlusion phase of the occlusion device positioning test. The method may also include, in response to detecting that the pulsatile pressure parameter is less than a minimum threshold value, outputting an alert via a user interface of the control system indicating a recommendation to reposition of the occlusion catheter in the coronary sinus.

In some embodiments of a system for treating heart muscle tissue, the system may include a coronary sinus occlusion catheter including a distal tip portion comprising an adjustable occlusion device. Also, the system may include a control system to selectively activate the occlusion device for substantially occluding the coronary sinus during occlusion phases, and to deactivate the occlusion device for substantially non-occluding the coronary sinus during release phases. The control system may include a sensor signal input to receive a pressure sensor data signal indicative of a pressure in the coronary sinus at least during the occlusion phases. The control system may be optionally configured to determine, in response to stored data points of the pressure sensor data signal during each of the occlusion phases, a cumulative dosage value. The control system can include a display unit that optionally shows the calculated cumulative dosage value, an estimated amount of salvaged heart muscle tissue based upon the calculated cumulative dosage value, or both.

In other embodiments, a method may include receiving a pressure sensor data signal indicative of a coronary sinus pressure after a occlusion catheter has substantially occluding the coronary sinus during an occlusion phase in a sequence of multiple occlusion phases. The method may also include storing data in a computer-readable memory device of a control console indicative of at least pressure maxima and pressure minima measured during the sequence of multiple occlusion phases. The method may further include, after each occlusion phase in the sequence of multiple occlusion phases, calculating a cumulative dosage value indicative of a measurement of progress of reducing an infarct size. The cumulative dosage value may be calculated based at least in part upon the data the pressure maxima and pressure minima measured during the sequence of multiple occlusion phases. The method may also include, after each occlusion phase in the sequence of multiple occlusion phases, updating a display of: the calculated cumulative dosage value presented on a display device of the control console, an estimated amount of salvaged heart muscle tissue based upon the calculated cumulative dosage value, or both.

In particular embodiments described herein, a system for treating heart muscle tissue may include a coronary sinus occlusion catheter including a distal tip portion comprising an adjustable occlusion device. Also, the system may include a control system to selectively activate the occlusion device for substantially occluding the coronary sinus during occlusion phases, and to deactivate the occlusion device for substantially non-occluding the coronary sinus during release phases. The control system may include a sensor signal input to receive a pressure sensor data signal indicative of a pressure in the coronary sinus at least during the occlusion phases. Optionally, the control system may be configured to, in response to stored data points of the pressure sensor data signal during at least one of the occlusion phases, output an alert via a user interface of the control system indicating a recommendation to reposition of the occlusion device of the coronary sinus occlusion catheter.

In some embodiments, a method may include receiving a pressure sensor data signal indicative of a coronary sinus pressure after a occlusion catheter has substantially occluding the coronary sinus during an occlusion phase of an occlusion device positioning test. The method may further include storing data in a computer-readable memory device of an occlusion device control system indicative of at least pressure maxima and pressure minima measured during the sequence of multiple occlusion phases. The method may also include, after the occlusion phase of the occlusion device positioning test, calculating a pulsatile pressure parameter. The pulsatile pressure parameter may be calculated based at least in part upon the data the pressure maxima and pressure minima measured during the occlusion phase of the occlusion device positioning test. The method may further include, in response to detecting that the pulsatile pressure parameter is less than a minimum threshold value, outputting an alert via a user interface of the control system indicating a recommendation to reposition of the occlusion catheter in the coronary sinus.

Some of the embodiments described herein may provide one or more of the following benefits. First, particular embodiments of the control system and catheter device can operate to intermittently occlude the coronary sinus or other heart vessel for controlled periods of time that provide effective redistribution of blood flow toward ischemic or otherwise damaged heart muscle tissue. The controlled periods of time may be accurately calculated by the control system based upon the input signals (for instance, the coronary sinus pressure) detected using the catheter device or another sensor device for use with the heart.

Second, some embodiments of the control system and catheter device can be configured to execute an occlusion device positioning test, preferably during the initiation of the coronary sinus occlusion process, to output a user interface communication indicative of whether the occlusion device of the catheter is positioned within the coronary sinus to provide a satisfactory level of redistributed blood flow. In some circumstances, when the occlusion device positioning test indicates an unsatisfactory level of occlusion is detected (e.g., in response to monitoring a differential between the systolic and diastolic pressures in the coronary sinus during an occlusion phase), the control system can output a message via a user interface of the control system indicative of suggested actions to improve the level of occlusion. Such corrective actions suggested via the user interface of the control system can include repositioning the catheter device in relation to the coronary sinus, or switching out the catheter device to a different catheter device that has a different size or shape, or the like. After implementing corrective actions, the occlusion device positioning test can be repeated to until the control system confirms (e.g., via the user interface of the control system) that the occlusion device is positioned within the coronary sinus to provide a satisfactory level of redistributed blood flow.

Third, particular embodiments of the control system can be configured to monitor one or more patient characteristics when the catheter device is activated and deactivated over a period of successive occlusion phases in the coronary sinus, and can also be configured to calculate a cumulative dosage value indicative of a treatment level that has been administered to a patient over the course of the successive occlusion phases. Such monitored patient characteristics can include, for example, one or more of: (i) the differential between the systolic and diastolic pressures during the occlusion phase, (ii) the differential between the systolic pressure plateau of the occlusion phase and the average non-occluded pressure, and (iii) the inflation hold time of the occlusion phase. In one non-limiting example, the control system can be configured to determine, in response to stored data points of the coronary sinus pressure measurement during each of the occlusion phases, the cumulative dosage value in units of Pressure$^3$×time (as described in more detail below). The cumulative dosage value, which in some embodiments herein is referred to as a "PICSO Quantity," can be displayed on the user interface of the control system as a numerical value that is repeatedly updated with each new occlusion phase.

Fourth, in some embodiments, the cumulative dosage value determined by the control system can be used to reasonably estimate an amount of AAR heart tissue that has been salvaged over the course of the successive occlusion phases. As such, some embodiments of the control system can be configured to correlate the cumulative dosage value over the course of a PICSO treatment with an estimated efficacy value of the PICSO treatment, which may be optionally displayed via the user interface of the control system. For example, in some embodiments the system can calculate and display an estimated myocardial salvage index (MSI) that indicates how much of a heart tissue area at risk for ischemia has been salvaged as a result of the successive occlusion phases occurring during the PICSO treatment. In such circumstances, the control system can output to the user a numerical estimate of the treatment efficacy, which is optionally updated in real-time with each new occlusion phase and thereby can be used by the practitioner to make an informed decision on when the PICSO treatment process should be ceased.

Fifth, in particular embodiments the control system can be configured to provide clinician operators with additional types of information by which improved patient outcomes can be achieved. For example, the display of the PICSO Quantity, the estimated MSI based at least in part on the calculation of the PICSO Quantity, or a combination thereof during administration of the PICSO treatment can facilitate the administration of an effective and satisfactory level of treatment by which improved patient outcomes can be achieved.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3 is a partial cross-sectional view of a catheter device and a guide member of the system of FIG. 1.

FIG. 4 is a side view of a portion of the catheter device of FIG. 3.

FIG. 5 is a transverse cross-sectional view of a shaft portion the catheter device of FIG. 3.

Like reference symbols in the various drawings indicate like elements.

DETAILED DESCRIPTION OF ILLUSTRATIVE EMBODIMENTS

Figure 1:
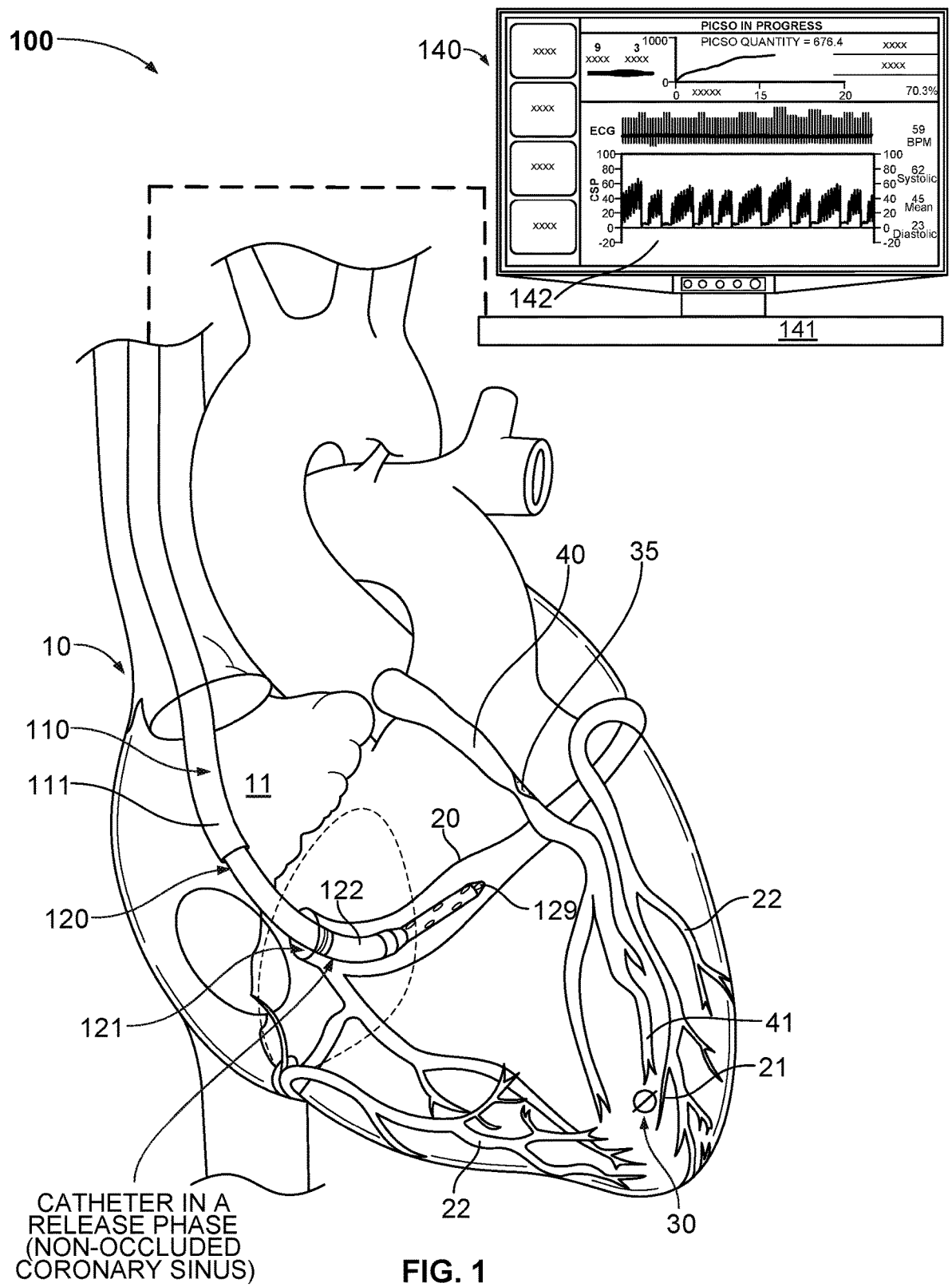
FIG. 1 is a perspective view of a system for treating heart tissue, including a catheter device in a non-occluding configuration within the coronary sinus of a heart, in accordance with some embodiments.
Figure 2:
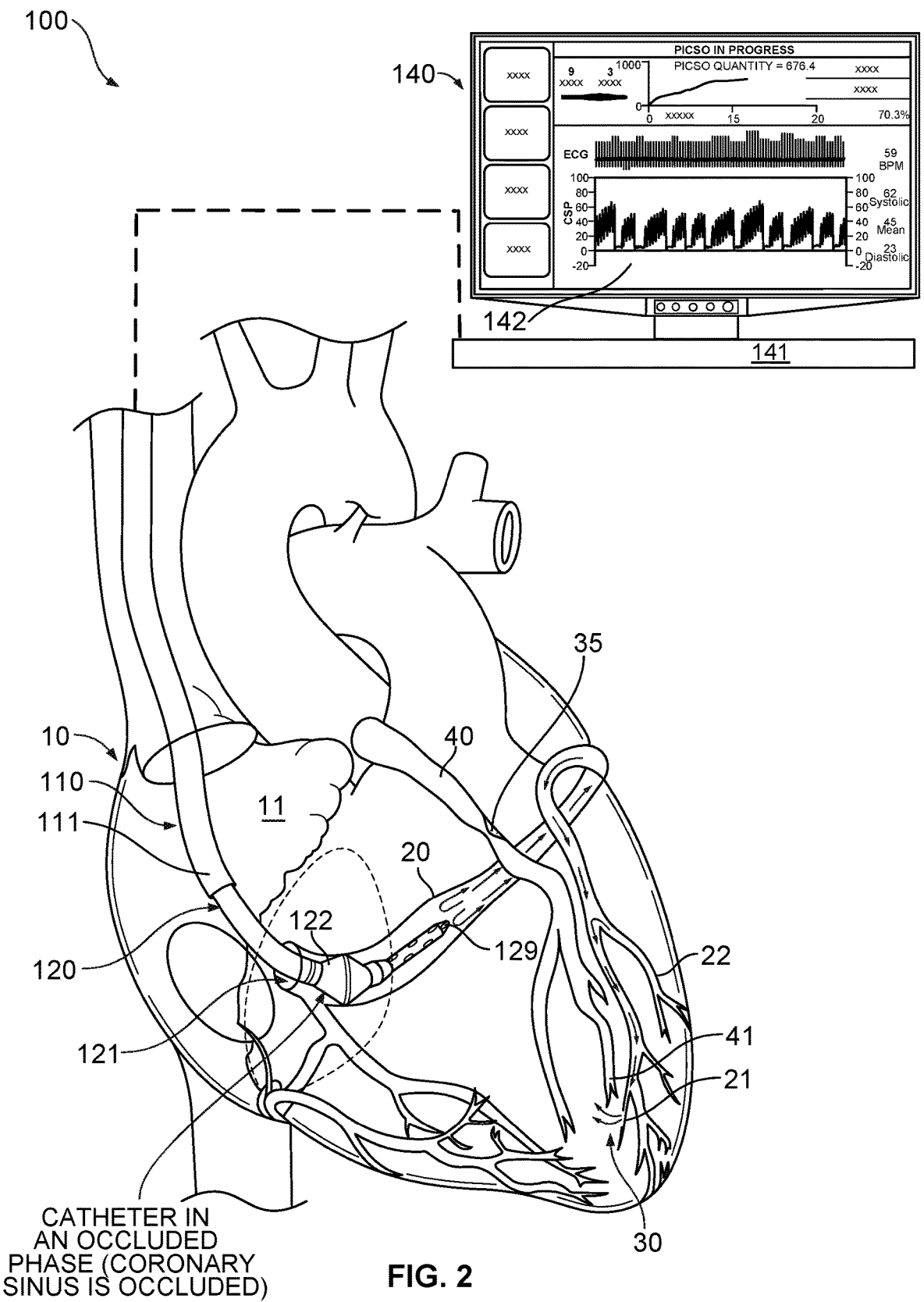
FIG. 2 is a perspective view of the system of FIG. 1, including the catheter device in an occluding configuration, in accordance with some embodiments.

Referring to FIGS. 1-2, some embodiments of a system 100 for treating heart tissue can include a coronary sinus occlusion catheter 120 and a control system 140 configured to activate the coronary sinus occlusion catheter 120 to intermittently occlude a coronary sinus 20 of a heart 10. The catheter 120 can be configured to adjust between a non-occluding position (FIG. 1) and an occluding position (FIG. 2) so as to intermittently occlude the coronary sinus and thereby redistribute venous blood flow toward heart muscle tissue 30. In this embodiment, the coronary sinus occlusion catheter 120 includes a distal tip portion 121 and a proximal portion 131 (FIG. 6), which includes a proximal hub 132 configured to connect with an external control system 140 (FIG. 6) via a number of fluid or sensor lines. As described in more detail below, the control system 140 may be employed to operate one or more components at the distal tip portion 121 of the coronary sinus occlusion catheter 120 while also receiving one or more sensor signals that provide data indicative of a heart performance parameter (e.g., coronary sinus pressure, electrocardiogram (ECG) information, or another measured parameter indicative of hemodynamic performance of the heart). In some embodiments, the control system 140 is configured to control the catheter 120 so as to occlude the coronary sinus in accordance with a specific algorithm for determining a release time for releasing an occlusion phase based at least in part upon data input from a sensor. In particular embodiments, as described further below, the control system 140 is configured to calculate a cumulative dosage value indicative of the cumulative effects of the successive occlusion phases, and furthermore a user interface 142 of the control system can then display the cumulative dosage value (sometimes referred to herein as the "PICSO Quantity"), the Estimated MSI based at least in part on the calculation of the PICSO Quantity, or both. These values determined and output by the control system 140 during the PICSO treatment can be optionally updated in real-time with each new occlusion phase, thereby providing the practitioner with medically pertinent information that aids the practitioner in deciding when the PICSO treatment should be ceased.

Briefly, in use, the distal tip portion 121 of the coronary sinus occlusion catheter 120 can be arranged in a coronary sinus 20 of a heart 10 and thereafter activated to intermittently occlude the blood flow exiting from the coronary sinus 20 and into the right atrium 11. During such an occlusion of the coronary sinus 20, the venous blood flow that is normally exiting from the coronary sinus 20 may be redistributed into a portion of heart muscle tissue 30 that has been damaged due to blood deprivation or loss of functional myocardium. For example, the portion of heart muscle tissue 30 can suffer from a lack of blood flow due to a blockage 35 in a coronary artery 40. As a result, the arterial blood flow to the affected heart muscle tissue 30 via a local artery 41 can be substantially reduced such that the heart muscle tissue 30 becomes ischemic or otherwise damaged. Further, because the arterial blood flow is reduced, the venous blood flow exiting from the local vein 21 is likewise reduced. Other branch veins 22 located at different regions along the heart 10 may continue to receive blood flow, thereby creating a supply of venous blood flow exiting through the coronary sinus 20. In some embodiments, the coronary sinus occlusion catheter 120 can be delivered into the coronary sinus 20 and thereafter activated so as to intermittently occlude the coronary sinus 20 (refer to FIG. 2). Such an occlusion can cause the venous blood flow to be redistributed to the local vein 21 and then into the portion of heart muscle tissue 30 that suffers from a lack of blood flow due to the blockage 35 in the coronary artery 40. As such, the ischemic or otherwise damaged heart muscle tissue 30 can be treated with the redistributed venous blood flow so that the heart muscle tissue 30 receives an improved supply of nutrients. (As shown in FIGS. 1-2, the catheter 120 is deployed into the coronary sinus 20 before the arterial blockage 35 is repaired or removed to restore normal coronary arterial blood flow. However, in alternative embodiments, the arterial blockage 35 can be repaired or removed immediately before or contemporaneously during use of the catheter 120 to occlude the coronary sinus 20.)

Still referring to FIGS. 1-2, the system 100 may optionally include a guide member 110 that is advanced through the venous system of the patient and into the right atrium 11. The guide member 110 in this embodiment comprises a guide sheath having a lumen extending between a distal end 111 (FIG. 1) and a proximal end 112 (FIG. 4). In alternative embodiments, the guide member 110 can serve as guidance for a guide wire having an exterior surface extending between the distal end and the proximal end. Optionally, the guide member 110 includes a steerable mechanism to control the orientation of the distal end so as to steer the distal end 111 through the venous system and into the right atrium 11. Also, the guide member 110 can include one or more marker bands along the distal end 111 so that the position of the distal end can be monitored during advancement using an imaging device.

After the guide member 110 is advanced into the right atrium 11, the distal end 111 may be temporarily positioned in the coronary sinus 20 or the coronary sinus ostium. From there, the distal tip portion 121 of the coronary sinus occlusion catheter 120 can be slidably advanced along the guide member 110 for positioning inside the coronary sinus 20. In the embodiments in which the guide member 110 comprises a guide sheath, the distal tip portion 121 of the coronary sinus occlusion catheter 120 can slidably engage with an interior surface of the lumen during advancement toward the coronary sinus 20. In the alternative embodiments in which the guide member 110 comprises a guide wire structure, the distal tip portion 121 of the coronary sinus occlusion catheter 120 can slidably advance over the exterior surface of the guide wire (e.g., a lumen 125 of the catheter 120 passes over the guide wire) during advancement toward the coronary sinus 20. After the coronary sinus occlusion catheter 120 reaches the coronary sinus 20, the distal end 111 of the guide member 110 can be withdrawn from the coronary sinus 20 and remain in the right atrium 11 for mechanical support during use of the coronary sinus occlusion catheter 120.

Figure 6:
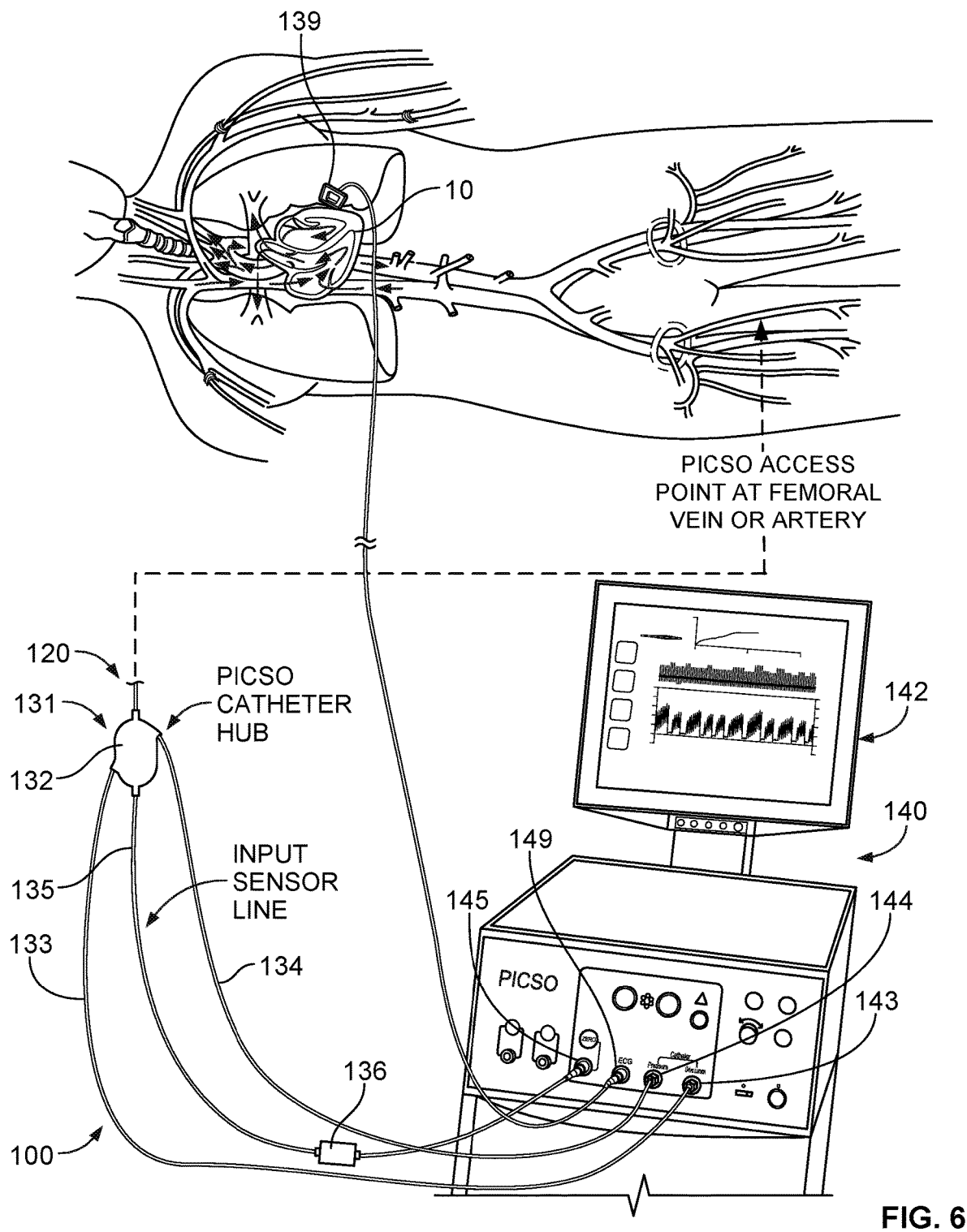
FIG. 6 is a perspective view of a portion of the system of FIG. 1.

Still referring to FIG. 1, the distal tip portion 121 of the coronary sinus occlusion catheter 120 that is positioned in the coronary sinus 20 includes an occlusion device 122, which in this embodiment is in the form of an inflatable balloon device. The occlusion device 122 can be activated so as to occlude the coronary sinus 20 and thereby cause redistribution of the venous blood into the heart muscle tissue 30 that is damaged due to a lack of arterial blood flow. As described in more detail below, the inflatable balloon device 122 can be in fluid communication with an internal lumen of the coronary sinus occlusion catheter 120, which is in turn in communication with a pneumatic subsystem of the control system 140 (FIG. 6). As such, the control system 140 can be employed to inflate or deflate the balloon device 122 in the coronary sinus.

The distal tip portion 121 also includes a one or more distal ports 129 that are positioned distally forward of a distal end of the occlusion device 122. In the depicted embodiments, the distal ports 129 as defined along a flexible elongate shaft portion that extends distally forward of a distal end of the occlusion device 122, and a majority or all of the distal ports face is a generally radially outward direction and are substantially uniformly spaced apart from one another along the circumference of the distal tip. As described in more detail below, the distal ports 129 may all be in fluid communication with a single sensor lumen (FIG. 5) extending through the coronary sinus occlusion catheter 120. Accordingly, at least one parameter of the coronary sinus (e.g., the coronary sinus pressure or other parameters indicative of hemodynamic performance as described below) can be monitored via a sensor device in communication with the distal ports 129.

Figure 7:
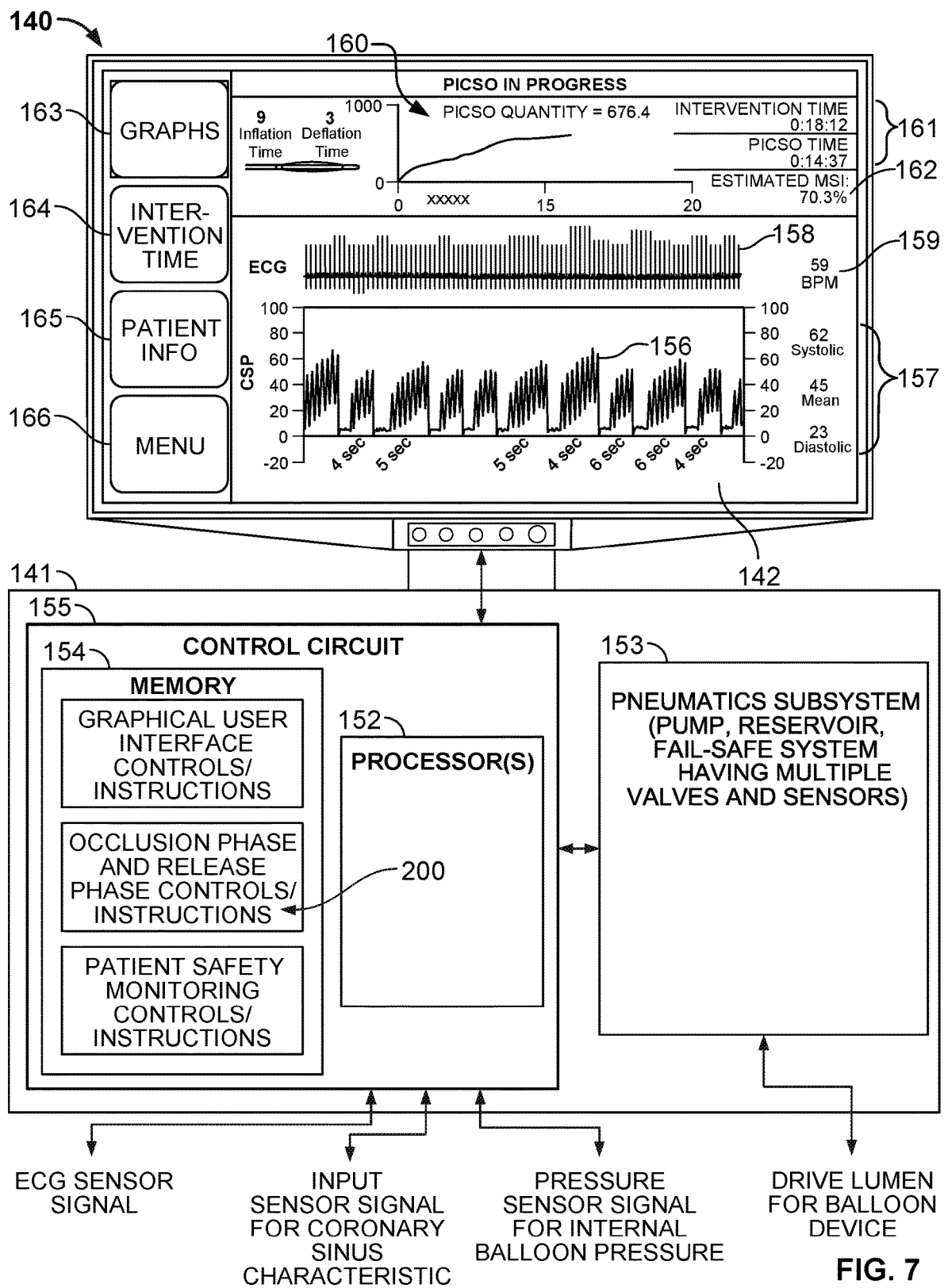
FIG. 7 is a diagram of a control system of the system of FIG. 6.

Referring now to FIGS. 3-5, the coronary sinus occlusion catheter 120 carries the occlusion device 122 along its distal tip portion 121 while the proximal hub 132 is arranged along the proximal portion 131. As previously described, the proximal hub 132 serves as the connection interface between a number of fluid or sensor lines 133, 134, and 135 (FIG. 3) and the corresponding lumens 123, 124, and 125 (FIG. 5) extending through the catheter 120. In this embodiment depicted in FIG. 3, the sensor line 135 is positioned as a central lumen 125 extending through the catheter 120. The sensor line 135 can be configured to communicate an input signal indicative of a measured parameter in the coronary sinus to the control system 140 (FIGS. 6-7). For example, the sensor line can be equipped with a sensor device (e.g., mounted near the distal ports 129) or otherwise equipped with a communication path between the distal ports 129 and the control system 140. As such, the catheter 120 can be configured to communicate at least one input signal indicative of a measured parameter in the coronary sinus, such as a fluid pressure (e.g., the coronary sinus pressure), a fluid temperature (e.g., using a temperature sensor positioned near the distal ports 129 and connected to the control system 140 via the sensor line 135), a volume or mass flow rate or rate of change thereof (e.g., using a flow sensor positioned near the distal ports 129 and connected to the control system 140 via the sensor line 135), an acceleration of the coronary sinus vessel (e.g., using one or more accelerometers positioned along the distal tip and connected to the control system 140 via the sensor line 135), a displacement of the coronary sinus vessel (e.g., using an ultrasound or optical measuring device to detect the movement of the coronary sinus vessel during each heartbeat), or another parameter indicative of hemodynamic performance of the heart (e.g., intra coronary sinus or other intra vessel electrocardiogram (ECG), contractility measurements, or the like).

In this particular embodiment, the sensor line 135 of the catheter 120 is configured to detect the coronary sinus pressure, which can be accomplished using a pressure sensor positioned near the distal ports 129 or using a fluid-filled path through the sensor line 135. For example, at least the sensor line 135 is connected to the proximal hub 132 using a Luer lock 137 so as to maintain the fluid path from the central lumen 125 of the catheter 120 to the lumen of the line 135.

As previously described, the system 100 may include the guide member 110 that is used to direct the coronary sinus occlusion catheter 120 through the venous system and into the heart 10. Referring to FIG. 3, the guide member 110 may be a guide sheath having a central lumen extending from a proximal end 112 (FIG. 4) to a distal end 111 (FIG. 1.) As previously described, the guide member 110 may be equipped with a steering mechanism (e.g., steel cables, a shape memory element, or the like) so that the practitioner can more readily advance the guide member 110 through the venous system and into the right atrium.

Still referring to FIGS. 3-5, the occlusion device 122 of the coronary sinus occlusion catheter 120 may comprise an inflatable balloon device having a predetermined shape when in the inflated condition. In this embodiment, the inflatable balloon device 122 includes a first conical portion narrowing down toward the distal direction, a second conical portion narrowing down toward the proximal direction, and a small generally cylindrical rim portion which is arranged between the conical portions. The narrowed ends of each of the conical portions are connected with the catheter shaft so as to provide a seal that prevents gas leakage from the balloon device 122. In the inflated condition, the diameter of the balloon device 122 in the region of the cylindrical rim portion is, for example, between about 6 mm and about 40 mm, between about 7 mm and about 25 mm, and preferably about 15 mm. The longitudinal length of the balloon device is, for example, between about 20 mm and about 30 mm, and preferably about 25 mm. Optionally, the coronary sinus occlusion catheter 120 can be equipped with one or more marker bands positioned inside the balloon device 122 so as to be rendered visible during an interventional procedure by suitable imaging processes.

As shown in FIG. 5, the shaft of the coronary sinus occlusion catheter 120 extending distally from the proximal hub 132 can include a plurality of lumens 123, 124, 125, and 126. In this embodiment, the ring segment-shaped lumen 123 serves to supply and discharge fluid (e.g. helium or carbon dioxide gas in this embodiment) for inflating and evacuating the balloon device 122. The ring segment-shaped lumen 124, which is smaller than the other lumen 123, likewise communicates with the interior of the balloon device 122 and serves to measure the fluid pressure within the balloon device 122. The central lumen 125 in this embodiment is employed for measuring the coronary sinus pressure. The central lumen 125 is in fluid communication with the distal ports 129 of the catheter 125 so that the blood pressure in the coronary sinus is transferred to the fluid-filled path extending through the central lumen 125 and to the pressure sensor device 136 (FIG. 2). Alternatively, a miniature pressure sensor can be positioned immediate adjacent to the distal ports 129 such that a sensor wire (e.g., electrical or optical) extends through the central lumen 125 for communication with the control system 140 (FIG. 2). In this embodiment, the shaft of the coronary sinus occlusion catheter 120 includes a fourth lumen 126 having a circular cross section. One or more additional sensors or sensor wires can be positioned in this fourth lumen. Alternatively, a stiffening wire can be arranged in the fourth lumen 126 so as to extend through the catheter shaft in the region of the balloon device 122. The stiffening wire, which can comprise of a shape memory material such as Nitinol or can comprise piezo steering/stiffening elements, can be used to facilitate delivery of the distal tip portion 121 into the coronary sinus 20.

Referring to FIG. 4 in more detail, the distal ports 129 of the catheter 120 are arranged distally forward of the distal end of the balloon device 122 and are oriented to face generally radially outward from the end of the catheter 120. In the depicted embodiments, the distal ports 129 as defined along a flexible elongate shaft portion that extends distally forward of a distal end of the occlusion device 122, and optionally, the flexible elongate shaft portion that carries the distal ports 129 may extend for a longitudinal length that is greater than the longitudinal length of the balloon device 122. As such, the distal ports 129 of the coronary sinus occlusion catheter 120 can be configured so that the fluid pressure in the coronary sinus can be accurately measured even if a portion of the distal end abuts against the wall of the coronary sinus or any other vessel. In this embodiment, the distal ports 129 comprise three or more ports that are evenly spaced apart along the flexible elongate shaft portion and along a tapered tip, thereby enabling the fluid pressure in the coronary sinus to be applied into one or more of the ports 129 even if some of the ports 129 are positioned against a wall of the coronary sinus.

Referring now to FIGS. 6-7, the control system 140 can be configured to provide automated control of the occlusion device 122 of the coronary sinus occlusion catheter 120. In some embodiments, the control system 140 includes a computer processor that executes computer-readable instructions stored on a computer memory device so as to activate or deactivate the occlusion in the coronary sinus 20 in accordance with a particular process. For instance, the control system 140 can be configured to release the occlusions phase (e.g., deflate the occlusion balloon 122 in this embodiment) in the coronary sinus 20 in response to a series of real-time measurements (e.g., coronary sinus pressure measurements in this embodiment) detected during the same occlusion phase. In addition, the control system 140 is equipped with a display device 142 having a graphical user interface that provides a practitioner or other users with time-sensitive, relevant data indicative of the progress of a coronary sinus occlusion procedure and the condition of the heart 10. As such, the user can readily monitor the patient's condition and the effects of intermittently occluding the coronary sinus 20 by viewing the graphical user interface 142 while contemporaneously handling the coronary sinus occlusion catheter 120 and other heart treatment instruments (e.g., angioplasty catheters, stent delivery instruments, or the like). Additionally, the control system 140 in this embodiment is configured to calculate a cumulative dosage value indicative of the cumulative effects of redistributing blood flow over the course of successive occlusion phases. Preferably, the cumulative dosage value calculated by the control system 140 is useful in estimating an amount of AAR heart tissue that has been salvaged over the course of the successive occlusion phases. In such embodiments, the user interface 142 of the control system 140 can then display the cumulative dosage value, the Estimated MSI based at least in part on the calculation of the cumulative dosage value, or both. These values output by the control system 140 during the PICSO treatment can be updated and displayed with each new occlusion phase, thereby providing the practitioner with medically pertinent, time-sensitive information that aids the practitioner in deciding when the PICSO treatment should be ceased.

As shown in FIG. 6, the proximal portion 131 of the coronary sinus occlusion catheter 120 and the control system 140 are positioned external to the patient while the distal tip portion 121 is advanced into the coronary sinus 20. The proximal portion 131 includes the proximal hub 132 that is coupled to the control system 140 via a set of fluid or sensor lines 133, 134, and 135. As such, the control system 140 can activate or deactivate the occlusion component 122 at the distal tip portion 121 of the coronary sinus occlusion catheter 120 while also receiving one or more sensor signals that provide data indicative of heart performance parameters (e.g., coronary sinus pressure, fluid temperature in the coronary sinus, volume or mass flow rate, rate of change of the volume or mass flow rate, acceleration of the coronary sinus vessel, displacement of the coronary sinus vessel, intra coronary sinus or other intra vessel electrocardiogram (ECG), surface electrocardiogram (ECG) information, contractility, or another measured parameter indicative of hemodynamic performance of the heart).

The proximal hub 132 of the coronary sinus occlusion catheter 120 serves to connect the plurality of fluid or sensor lines 133, 134, and 135 with the portion of the coronary sinus occlusion catheter 120 that extends into the patient's venous system. For example, the first line 133 extending between the control system 140 and the proximal hub 132 comprises a fluid line through which pressurized fluid (e.g., helium, another gas, or a stable liquid) can be delivered to activate the occlusion component (e.g., to inflate the inflatable balloon device 122). The fluid line 133 is connected to a corresponding port 143 of the control system 140 (e.g., the drive lumen port in this embodiment) so that the line 133 is in fluid communication with the pneumatic subsystem 153 housed in the control system 140 (as shown in FIG. 7). The proximal hub 132 joins the first line 133 with a balloon control lumen 123 (FIG. 5) extending through the coronary sinus occlusion catheter 120 and to the inflatable balloon device 122.

In another example, the second line 134 extending between the control system 140 and the proximal hub 132 comprises a balloon sensor line that is in fluid communication with the interior of the inflatable balloon device 122 so as to measure the fluid pressure within the balloon device 122. The proximal hub 132 joins the second line 134 with a balloon pressure lumen 122 (FIG. 5) extending through the coronary sinus occlusion catheter 120 and to the inflatable balloon device 122. The pressure of the balloon device 122 may be monitored by an internal control circuit 155 (FIG. 7) of the control system 140 as part of a safety feature that is employed to protect the coronary sinus 20 from an overly pressurized balloon device. The balloon sensor line 134 is connected to a corresponding port 144 of the control system 140 so that a pressure sensor arranged within the control system 140 can detect the fluid pressure in the balloon device 122. Alternatively, the pressure sensor may be arranged in the distal tip portion 121 or the in the proximal hub 132 such that only a sensor wire connects to the corresponding port 144 of the control system 140.

The proximal hub also connects with a third line 135 extending from the control system 140. As previously described, the third line can serve as the sensor line that is employed to communicate an input signal (as described above) to the control system 140. In this particular embodiment, the third line 135 comprises a coronary sinus pressure line that is used to measure the fluid pressure in the coronary sinus both when the balloon device 122 is inflated and when it is deflated. The proximal hub 132 joins the third line 135 with a coronary sinus pressure lumen 125 (FIGS. 4-5) extending through the coronary sinus occlusion catheter 120 and to the distal ports 129 that are forward of the balloon device 122. In this embodiment, the coronary sinus pressure lumen 125 and at least a portion of the third line 135 may operate as fluid-filled path (e.g., saline or another biocompatible liquid) that transfers the blood pressure in the coronary sinus 20 to pressure sensor device 136 along a proximal portion of the third line 135. The pressure sensor device 136 samples the pressure measurements (which are indicative of the coronary sinus pressure) and outputs an sensor signal indicative of the coronary sinus pressure to the corresponding port 145 of the controller system 140 for input to the internal control circuit 155 (FIG. 7). As described in more detail below, the coronary sinus pressure data are displayed by the graphical user interface 142 in a graph form 156 (refer to FIG. 7) so that a practitioner or other users can readily monitor the trend of the coronary sinus pressure while the coronary sinus 20 is in an occluded condition and in an non-occluded condition. Optionally, the graphical user interface 142 of the control system 140 can also output a numeric pressure measurement 157 (refer to FIG. 7) on the screen so that the practitioner can readily view a maximum coronary sinus pressure, a minimum coronary sinus pressure, the mean coronary sinus value, or all values. In some alternative embodiments, the pressure sensor device 136 can be integrated into the housing of the control system 140 so that the third line 135 is a fluid-filled path leading up to the corresponding port 145, where the internal pressure sensor device (much like the device 136) samples the pressure measurements and outputs a signal indicative of the coronary sinus pressure. In further alternative embodiments, the third line 135 can include a fiber optic feed line, which extends from a fiber optic pressure sensor at least partially mounted in the catheter tip 129. This fiber optic feed line can be connected to a signal conditioning component (mounted in the catheter tip 129 or integrated into the housing of the control system 140), which may provide the signal conditioning for the optical pressure sensor).

Still referring to FIGS. 6-7, the system 100 may include one or more ECG sensors 139 to output ECG signals to the control system 140. In this embodiment, the system 100 includes a set of ECG sensor pads 139 (e.g., three sensor pads in some embodiments) that are adhered to the patient's skin proximate to the heart 10. The ECG sensors 139 are connected to the control system 140 via a cable that mates with a corresponding port 149 along the housing of the control system 140. As described in more detail below, the ECG data are displayed by the graphical user interface 142 in a graph form 158 (refer to FIG. 7) so that a practitioner or other user can readily monitor the patient's heart rate and other parameters while the coronary sinus is in an occluded condition and in an non-occluded condition. Optionally, the graphical user interface 142 of the control system 140 can also output numeric heart rate data 159 (refer to FIG. 7) based on the ECG sensor data so that the practitioner can readily view the heart rate (e.g., in a unit of beats per minute). The ECG sensor signals that are received by the control system 140 are also employed by the internal control circuit 155 (FIG. 7) so as to properly time the start of the occlusion period (e.g., the start time at which the balloon device 122 is inflated) and the start of the non-occlusion period (e.g., the start time at which the balloon device 122 is deflated). In addition, the control system may be equipped with additional ECG sensor signals capabilities to monitor the intra coronary, intra vessel or intra coronary sinus electrical ECG activity. These signals may be obtained from the coronary sinus occlusion catheter 120 measured at one or several locations alongside the shaft 139 or at the distal end where the distal ports 129 are located. Alternatively, or in addition, the ECG activity may be provided from another catheter in the heart such as the intra coronary ECG from an arterial vessel 40.

As shown in FIG. 7, some embodiments of the control system 140 include the internal control circuit subsystem 155 that communicates with the pneumatics subsystem 153. The control circuit subsystem 155 can include one or more processors 152 that are configured to execute various software modules stored on at least one memory device 154. The processors 152 may include, for example, microprocessors that are arranged on a motherboard so as to execute the control instructions of the control system 140. The memory device 154 may include, for example, a computer hard drive device having one or more discs, a RAM memory device, or the like that stored the various software modules.

In some embodiments, the memory device 154 of the control circuit subsystem 155 stores a graphical user interface software module including computer-readable instructions for controlling the graphical user interface 142. These graphical user interface control instructions may be configured to cause the interface 142 (which includes a touch screen display device in this embodiment) to display: the pressure data graph 156 indicative of the coronary sinus pressure, the coronary sinus pressure numerical data 157, the ECG data graph 158, the heart rate numerical data 159, a series of cumulative dosage values calculated after each successive occlusion phase (which can be used to provide the PICSO Quantity graph 160 described further in reference to FIG. 12), treatment timers 161, and an Estimated MSI value 162 (which can be updated after each new occlusion phase as described further in reference to FIG. 12). Optionally, the graphical user interface can be configured to display more than the three graphs 156, 158, and 160 on the screen. For example, in some embodiments, the graphical user interface can be configured to contemporaneously display four or more different graphs, such as the coronary sinus pressure graph 156, the ECG data graph 158, the PICSO Quantity graph 160, a fourth graph that depicts the arterial pressure as a function of time, and a fifth graph that illustrates another data output (e.g., the volume of blood flow).

Further, the graphical user interface control instructions stored in the control circuit subsystem 155 may be configured to cause the interface 142 to display a number of configurable touch screen buttons 163, 164, 165, and 166 that enable the practitioner or other user to select different menu options or to input patient information or other data. In addition, the graphical user interface 142 may be configured to utilize several of the data inputs to display unique determinants of the status of the procedure such as the PICSO Quantity graph 160 and the Estimated MSI 162, for example. This information may guide the user to understand when the heart is improving based on the therapy provided, and thus to understand when to terminate the therapy.

In addition, the graphical user interface control instructions stored in the control circuit subsystem 155 may be configured to cause the interface 142 to display a number of one or more alerts (e.g., refer to FIGS. 9A and 9B), which can be in the form of messages or codes. In some embodiments, the determination of which alert condition, if any, should be display can be completed by the patient safety monitoring software module stored on the memory device 154.

Still referring to FIG. 7, in some embodiments the occlusion phase and release phase software module 200 stored on the memory device 154 can include computer-readable instructions that, when executed by one of the processors 152 (such as an embedded PC), causes the pneumatic subsystem 153 to activate or deactivate the balloon device 122 at selected times. The control system 140 can be configured to calculate the time periods during which the coronary sinus is in an occluded state and in a non-occluded state and to calculate when each occlusion phase should begin and when each occlusion phase should end in order to achieve a maximum clinical benefit of the desired mode of action, namely, altered venous side blood flow that induces microcirculation in a targeted heart tissue. The control system 140 may take into account various monitored parameters, and make the timing determinations in real-time, such that timing of each cycle of the method may be appropriate in light of monitored parameters.

After the duration of time for the release phase is reached, the process may start a new occlusion phase. This cyclical process can continue for an extended period of minutes or hours, thereby resulting in numerous cycles of occlusion phases and release phases. Accordingly, in some embodiments, the coronary sinus occlusion catheter 120 (FIGS. 1-2) may continue to intermittently occlude the coronary sinus (FIGS. 1-2) to thereby redistribute the venous blood flow to the damaged portion of the heart muscle tissue 30. The overall duration of time for using the coronary sinus occlusion catheter 120 to provide the multiple occlusion phases may be determined by a practitioner viewing the pertinent data presented via the user interface 142, including the cumulative dosage value, the Estimated MSI (which can be based at least in part on the calculation of the cumulative dosage value), or both. In some embodiments the control circuit 155 can include computer-readable instructions stored on the memory device 154 that, when executed by one of the processors 152, calculates indicators of the status and efficacy of the procedure such as the PICSO Quantity graph 160 and the Estimated MSI 162. The calculation of the PICSO Quantity values and the Estimated MSI 162 will be described further below in reference to FIGS. 8A, 8B, and 11. Optionally, the practitioner may rely upon additional factors when determining the overall duration of time for using the coronary sinus occlusion catheter 120, including the trend of the input sensor signals (e.g., the trend of coronary sinus pressure measurements as displayed on the user interface 142 of FIG. 7 or a derivate thereof), a measurement of particular bio-markers present in the patient's blood (e.g., lactate (which increases in the event of ischemia), potassium (an indicator of ischemic tissue), and the like), or a combination thereof or another input signal.

The patient safety monitoring software module stored on the memory device 154 can include computer-readable instructions that, when executed by one of the processors 152, causes the control circuit subsystem 155 to detect if any of the system sensors (e.g., the pressure sensors) output a measurement that is outside of a selected safety range. For example, if the coronary sinus pressure signal input to the control system 140 indicates a coronary sinus pressure that is above a selected threshold, the control circuit subsystem 155 can cause the graphical user interface 142 to display an alert in the form of a textual message or an error code. Further, in some embodiments, the control circuit subsystem 155 may automatically cause the pneumatic subsystem to deflate the balloon device 122 so as to immediately reduce the high pressure in the coronary sinus 20.

Still referring to FIG. 7, the pneumatic subsystem 153 of the control system 140 can be configured to promptly inflate or deflate the balloon device 122 in response to the control circuit subsystem. In some embodiments, the pneumatic subsystem may include a reservoir containing pressured gas, such as helium or carbon dioxide, and a vacuum pump. The reservoir and the vacuum pump can be controlled by a set of valves and are monitored by a set of pressure sensors that feedback into the control circuit subsystem 155. In such circumstances, the pneumatic subsystem can be configured to inflate or deflate the balloon device 122 at the distal tip portion 121 of the coronary sinus occlusion catheter 120 in less than 1 second, less that about 0.6 seconds, and preferably less than about 0.4 seconds.

Figure 8B:
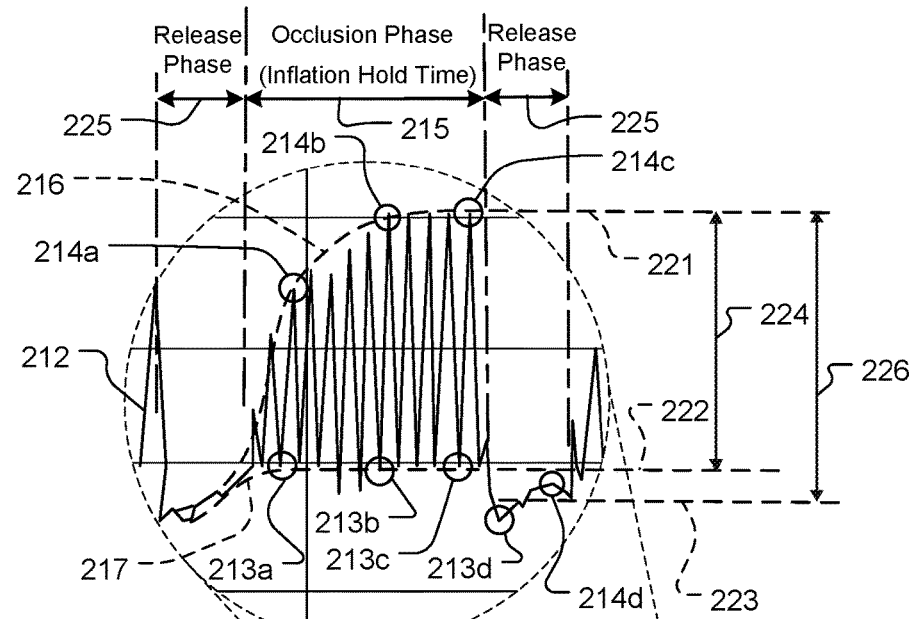
FIGS. 8A and 8B are examples of graphical plots of coronary sinus pressure values measured during heart tissue treatments using the system of FIG. 1.
Figure 8A:
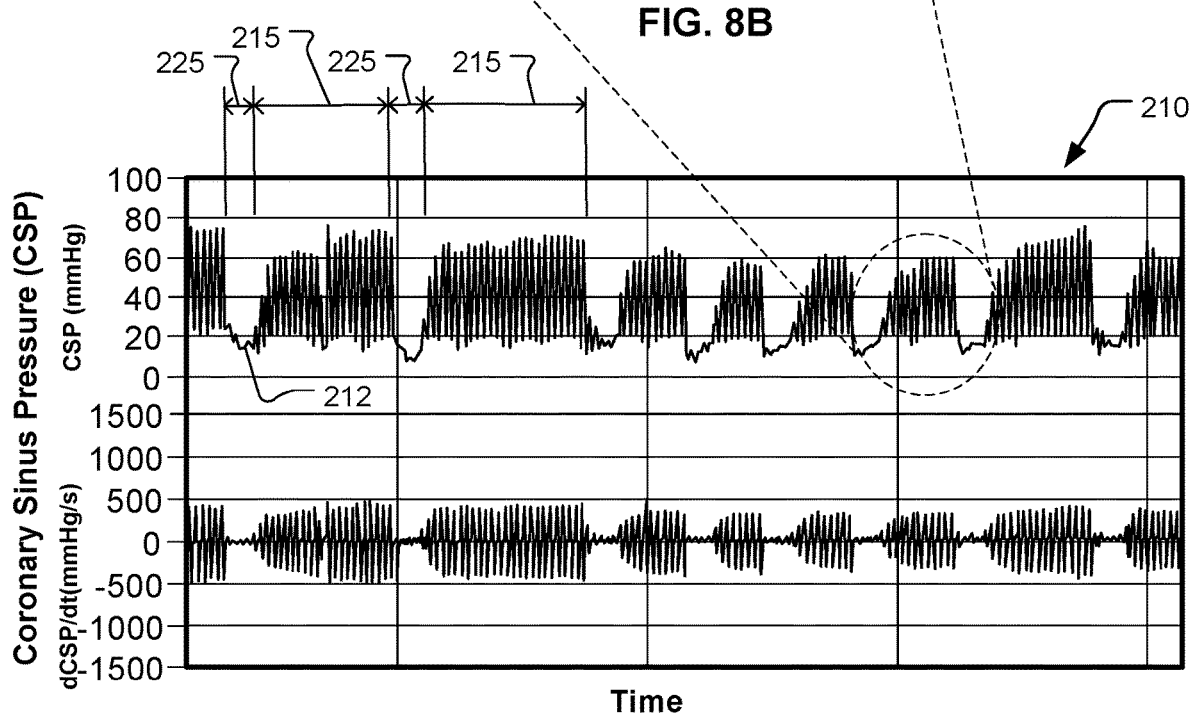

Referring now to FIGS. 8A and 8B, as mentioned above the control system 140 can be configured to receive data from a sensor signal input 212 (e.g., a coronary sinus pressure sensor, and the like) and to display on the graphical user interface 142 a graph of the data such as coronary sinus pressure graph 210. The upper plot on the graph 210 of FIG. 8A illustrates an example of the changes in coronary sinus pressure over time during a series of occlusion phases 215 and release phases 225. The lower plot of FIG. 8A illustrates the time-based derivative of the upper plot, which is the rate of the changes in coronary sinus pressure over time. FIG. 8B is an enlargement of an occlusion phase 215 that is bordered by preceding and succeeding release phases 225. As will be explained further below, in some embodiments the coronary sinus pressure data, from which graph 210 is created, can be used to: (i) confirm that the system 100 is attaining an effective and satisfactory level of occlusion so as to provide a desired quality of treatment and (ii) calculate a PICSO Quantity parameter that can be used to estimate an efficacy of the treatment in terms of an Estimated MSI (myocardial salvage index).

The control system 140 can be configured to monitor and store at least portions of the input signals from the sensors being used by the system 100. For example, in the embodiment depicted in FIGS. 8A and 8B, the control system 140 is configured to at least store the systolic maxima (e.g., pressure values such as data points 214a-d and the like) and the diastolic minima (e.g., pressure values such as data points 213a-d and the like) of the coronary sinus pressure signal 212 occurring over a series of consecutive heartbeats during each occlusion phases 215 and each release phases 225. Based at least partially upon the systolic maxima data points during the occlusion phase 215 (e.g., data points 214a-c), the control system 140 can be configured to perform a curve fitting operation so as to determine a "curve fit line" or "envelope" curve 216 for the pressure maxima occurring over a series of consecutive heartbeats during the occlusion phase 215. Similarly, based upon the diastolic minima data points during the occlusion phase 215 (e.g., data points 213a-c), the control system 140 can be configured to perform a curve fitting operation so as to determine a "curve fit line" or "envelope" curve 217 for the pressure minima occurring over a series of consecutive heartbeats during the occlusion phase 215. The curve fit lines 216 and 217 can define asymptote or plateau values of the systolic maxima and diastolic minima. For example, as illustrated in FIG. 8B, the systolic maxima curve fit line 216 defines a systolic plateau pressure 221. Similarly, the diastolic minima curve fit line 217 defines a diastolic plateau pressure 222.

The pressure difference between the systolic plateau pressure 221 and the diastolic plateau pressure 222 defines a parameter referred to herein as the "pulsatile pressure" 224. In this embodiment, the pulsatile pressure 224 occurring is the coronary sinus during each occlusion phase 215 can be calculated by the control system 140. Pressure pulses are generated by the heart beating, and higher pulsatile pressures 224 can be indicative of greater levels perfusion to the microcirculation of the damaged heart muscle tissue 30, which may result in more effective treatment over the course of successive occlusion phases 215. As will be described further below, the repeated redistribution of blood of the microcirculation of the damaged heart muscle tissue 30 can, in some circumstances, salvage or otherwise restore at least a portion of the myocardial area at risk (AAR) of infarction. In this embodiment, the salvage area can be quantifiably referred to by the myocardial salvage index (MSI). The efficacy of the treatment is also influenced by the duration of each occlusion phase 215. In this embodiment, the duration of each occlusion phase 215 is also referred to herein as the "inflation hold time," which is the period of time that the coronary sinus is substantially occluded by an activated occlusion device (e.g., in this embodiment, the inflated balloon device 122 of FIG. 2).

The control system 140 can also be configured to calculate a deflation average pressure 223 by averaging the systolic maxima and diastolic minima pressures detected during each release phase 225. For example, as shown in FIG. 8B, the diastolic minimum (e.g., data point 213d and the like) can be averaged with the systolic maximum (e.g., data point 214d and the like) during the release phase 225 to calculate a deflation average pressure 223. The deflation average pressure 223 is the average pressure in the coronary sinus during the release phase when the coronary sinus is not occluded. The difference between the systolic plateau pressure 221 and the deflation average pressure 223 is referred to herein as the global relative pressure drop 226.

When the occlusion of the coronary sinus is released (e.g., when transitioning from the occlusion phase 215 to the release phase 225), the blood flow that was blocked once again begins to flow in its natural direction, rather than tending to redistribute through one or more cardiac veins as during the occlusion phase 215. As the blood begins to flow during the release phase 225, a "washout effect" can take place in the myocardial areas that were retroperfused as a result of the occlusion phase 215. That is, cellular waste products from under-perfused areas of the myocardium that received perfusion as a result of the occlusion phase 215 can be washed away with the blood as it flows from those areas towards the coronary sinus at the start of and during the release phase 225. The washout effect may be accentuated by the global relative pressure drop 226. In some embodiments, the control system 140 can be configured to release the occlusion phase 215 at a particular time point within a single heartbeat that can provide a significant washout effect (e.g., to enhance the removal of cellular waste products after the coronary sinus returns to a non-occluded state). For example, the control system 140 can monitor the ECG signal 149 (FIGS. 6-7) so as to trigger the release of the occlusion phase 215 at a time point approximately during a peak contraction of the heart (e.g., during a systolic pressure maximum).

The control system 140 is configured to monitor and store the coronary sinus pressure measurements and (optionally) other bodily characteristics (e.g., ECG), which can be used by the control system 140 to determine the previously described parameters for each occlusion phase/release phase cycle, including: (i) systolic plateau pressure 221, (ii) pulsatile pressure 224, (iii) global relative pressure drop 226, and (iv) inflation hold time. Optionally, the inflation hold time can be separately monitored value that is not determined from the coronary sinus pressure measurements.

As described herein, the control system 140 can be configured to calculate a cumulative dosage value using the coronary sinus pressure measurement data. Preferably, the cumulative dosage value calculated by the control system 140 can be indicative of the cumulative effects of redistributing blood flow over the course of successive occlusion phases. In some embodiments, the cumulative dosage value calculated by the control system 140 is useful in estimating an amount of AAR heart tissue that has been salvaged over the course of the successive occlusion phases. In such embodiments, the user interface 142 of the control system 140 can then display the cumulative dosage value, the Estimated MSI based at least in part on the calculation of the cumulative dosage value, or both. These values output by the control system 140 during the PICSO treatment can be updated and displayed with each new occlusion phase, thereby providing the practitioner with medically pertinent, time-sensitive information that aids the practitioner in deciding when the PICSO treatment should be ceased.

The cumulative dosage value determined by the control system 140 can be calculated using a selected algorithm that provides a numerical value indicative of the cumulative effects of redistributing blood flow over the course of successive occlusion phases. For example, the cumulative dosage value determined by the control system 140 can provide a numerical expression of parameters referred herein as the "PICSO Quantity" as follows:

$$PICSO\ Quantity = \sum_{n=1}^{n=Total\ PICSO\ Cycles} (PPP_n \times GRPD_n \times IHT_n), \quad \text{Equation \#1}$$

where:
PPP=the pulsatile pressure,
GRPD=the global relative pressure drop, and
IHT=the inflation hold time.
The units of PICSO Quantity are units of (pressure)²×(time). For example, the units of PICSO Quantity can be "mmHg²-minutes" or the like. As previously described, the PICSO Quantity calculated by the control system 140 according to Equation #1 can be used to reasonably estimate the amount of AAR heart tissue that has been salvaged over the course of the successive occlusion phases. For instance, it is believed that in particular circumstances the PICSO Quantity value provides an approximately linear relationship with the Estimated MSI (as described in more detail below in connection with FIG. 11). In an alternative example, the cumulative dosage value determined by the control system 140 can provide a numerical expression of parameters referred herein as the "PICSO Quantity" as follows:

$$PICSO\ Dose = \sum_{n=1}^{n=Total\ PICSO\ Cycles} (SPP_n \times IHT_n), \quad \text{Equation \#2}$$

where:
SPP=the systolic plateau pressure, and
IHT=the inflation hold time;
The units of PICSO Dose are units of pressure multiplied by time. For example, the units of PICSO Dose can be "mmHg-minutes" or the like. In some circumstances, the PICSO value calculated by the control system 140 can be an indicator of an approximate amount of AAR heart tissue that has been salvaged over the course of the successive occlusion phases. It is envisioned that other combinations of the parameters provided herein can also be used to mathematically represent the extent and efficacy of the treatment provided by system 100.

In the depicted embodiments (FIGS. 1, 7, and 12), the control system 140 is configured to calculate and then display the PICSO Quantity value after each new occlusion phase 215, which can be output via the user interface 142 in numeric form, in a graphic plot form, or both (as shown in field 160). A practitioner viewing the user interface 142 is then enabled to use the PICSO Quantity value to enhance the practitioner's understanding of the efficacy of the treatment provided by system 100. In alternative embodiments, calculated value for PICSO Dose can be calculated and then display as an alternative, or in addition, to the PICSO Quantity value on the graphical user interface 142 of the system 100.

Figure 9A:
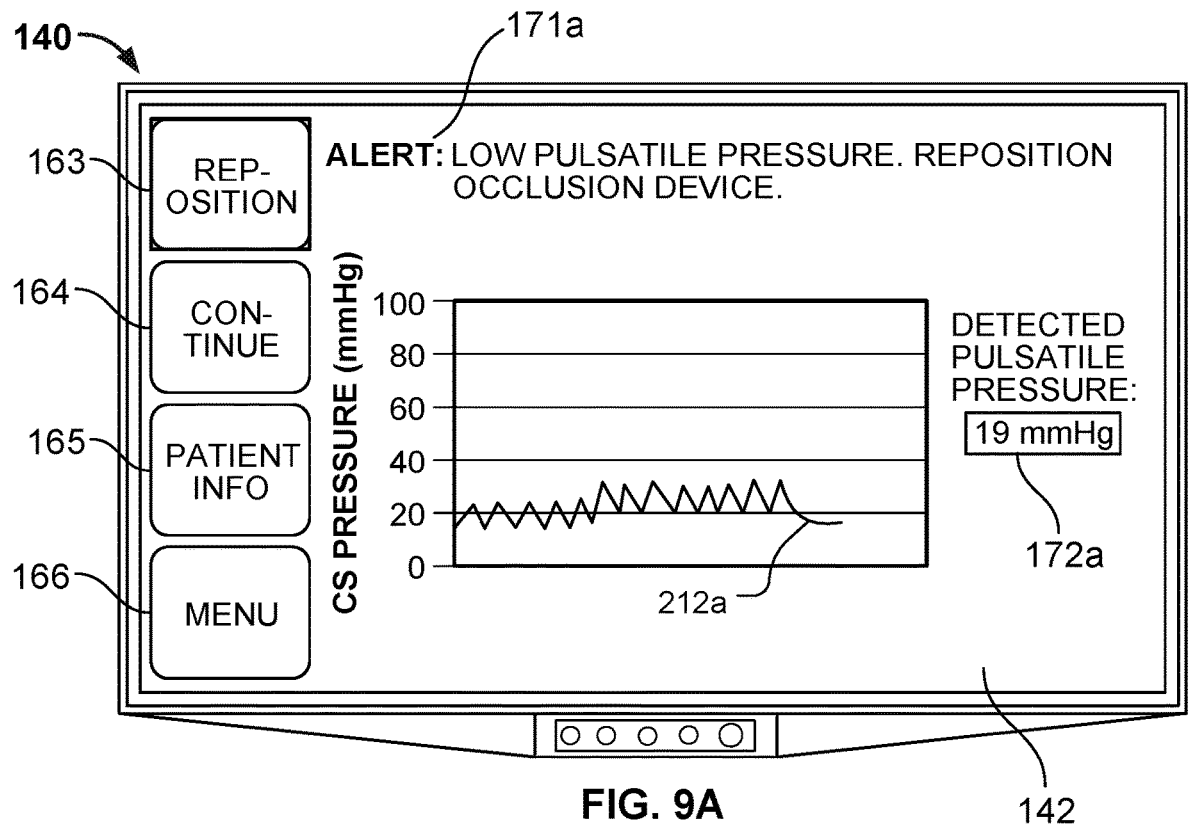
FIGS. 9A and 9B are front views of a portion of the control system of FIG. 1, including a graphical user interface of the system of FIG. 1 during an occlusion device positioning test.
Figure 9B:
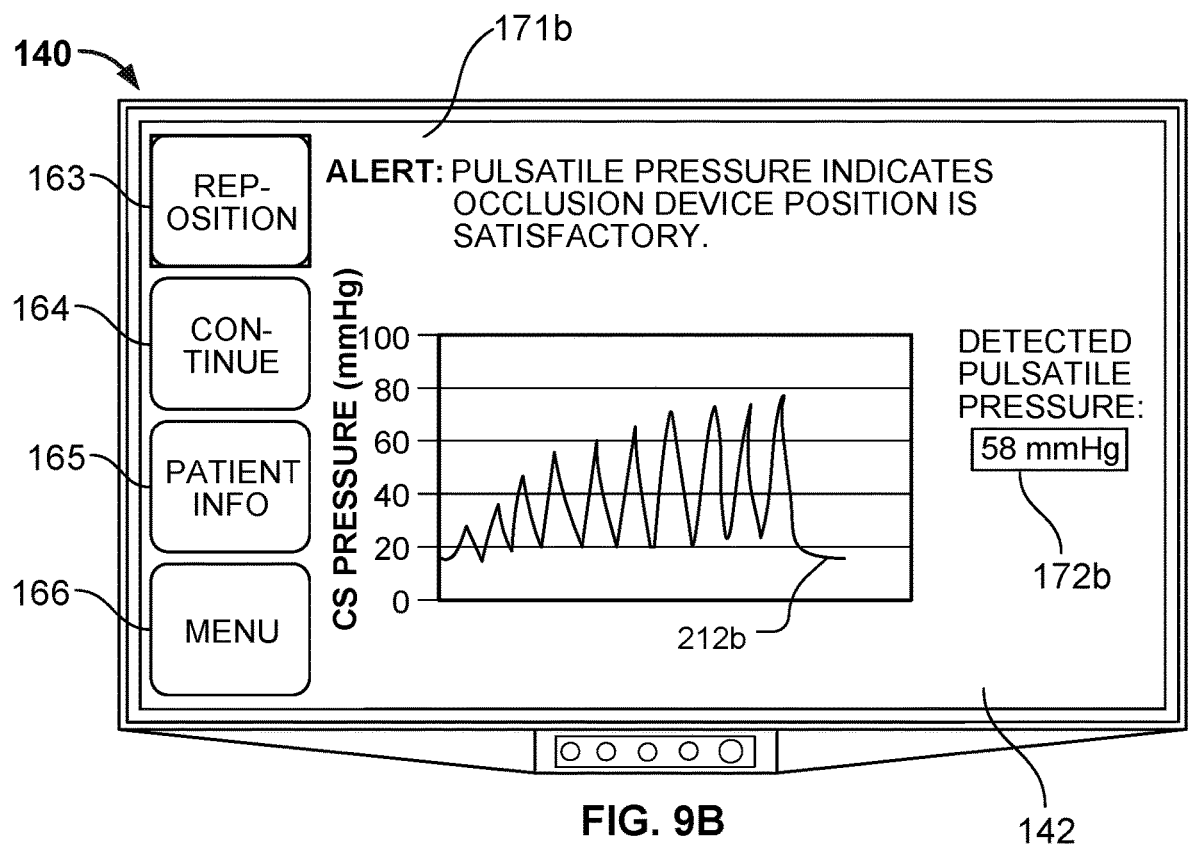

Referring to now FIGS. 9A and 9B, in some embodiments the control system 140 is configured to perform an occlusion device positioning test, for example, after the coronary sinus occlusion catheter is initially inserted into the coronary sinus and before the automated PICSO treatment process is initiated. The occlusion device positioning test can advantageously result in a confirmation or alert message output to the practitioner via the graphical user interface 142. This positioning step can be optionally performed to confirm whether a satisfactory level of occlusion during a sample occlusion phase is being achieved by the system 100. The level of occlusion, for example, can refer to the pressures (e.g., systolic maxima and pulsatile pressure) attained in the coronary sinus when the occlusion device 122 is inflated (refer to FIG. 2).

In the depicted embodiment of the system 100 (including the catheter device 120), the practitioner can attempt to position the occlusion device 122 near the ostium of the coronary sinus so that the periphery of the occlusion device 122 (when inflated) engages with the inner wall of the coronary sinus, thereby effectively redistributing the venous blood through the cardiac veins. The control system 140 can be configured to detect one or more patient characteristics (e.g., in this embodiment, coronary sinus pressure measurements during a sample occlusion phase) so as to determine whether the occlusion device 122 is located in a satisfactory position, and furthermore the control system 140 can be configured to alert the user with a suggestion to reposition the occlusion device 122 in some circumstances. For example, FIG. 9A depicts an example of when a desirable level of occlusion has not been attained and an alert message 171a is output from the control system 140. In another example, FIG. 9B depicts an example of when a desirable level of occlusion has been attained and a different alert message 171b is output from the control system 140 to confirm the satisfactory position of the occlusion device 122.

As described previously in connection with FIG. 8B, the efficacy of the treatment provided by system 100 can, in some circumstances, be affected by measurable pressure-based parameters such as the pulsatile pressure (the systolic plateau pressure minus the diastolic plateau pressure) and the global relative pressure drop (the systolic plateau pressure minus the deflation average pressure). Accordingly, after the catheter 120 is initially positioned in the coronary sinus and during an occlusion device positioning test, one or more cycles of occlusion can be performed to determine and display such parameters, and then the control system 140 can output a determination of whether the position of the occlusion device 122 is satisfactory. If the test cycle(s) indicates an unsatisfactory level of occlusion, the clinician operator may take corrective actions to improve the level of occlusion prior to continuing to administer the heart tissue treatment process using system 100. Such corrective actions can include repositioning the occlusion device in relation to the vessel, or switching out the occlusion device to a different occlusion device that has a different size or shape that may be more suitable to interface with the patient's anatomy. After implementing corrective actions, the occlusion device positioning test can be repeated to confirm whether an effective and satisfactory level of occlusion of the heart vessel has been attained, and if it has not been attained the clinician may again take corrective actions to improve the level of occlusion.

FIGS. 9A and 9B depict examples of the user interface display 142 of the control system 140 after the completion of running the occlusion device positioning test to confirm whether a satisfactory level of occlusion has been attained with the current position of the occlusion device 122 in the coronary sinus. FIG. 9A depicts an example of when a satisfactory level of occlusion has not been attained, and FIG. 9B depicts an example of when a satisfactory level of occlusion has been attained. Prior to running the occlusion device positioning test, the occlusion device is installed in the coronary sinus (or other vessel of the patient if the occlusion is intended for a different region of the body) and the system 100 is prepared to administer treatment to the heart tissue of the patient as described previously. As the occlusion device positioning test is executed by the control system 140, the occlusion device 122 is activated by the control system 140 (for either a predetermined period of time or for a variable period of time controlled by the measured pressure characteristics during the occlusion phase) and the sensor signal input 212a (e.g., a coronary sinus pressure sensor) is monitored by the control system 140 and displayed on the graphical user interface 142 for at least one occlusion cycle. Pressure parameters such as the systolic maxima and diastolic minima are monitored by the system 100 during the occlusion and release phases. From such monitored parameters, other parameters can be calculated (refer to FIG. 8B), such as the systolic plateau pressure, diastolic plateau pressure, pulsatile pressure 224, deflation average pressure 223, and the global relative pressure drop 226.

In some embodiments, at the completion of the occlusion device positioning test, the system 100 can compare the monitored and/or calculated pressure-based parameters to predetermined target threshold levels that are established at pre-selected values that represent a satisfactory level of occlusion. The following example is provided to illustrate this. In some embodiments a threshold level for the pulsatile pressure 224 may be established at a minimum threshold value. The minimum threshold value for the pulsatile pressure 224 may be a numeric value selected from a range of 25 mmHg or greater, about 25 mmHg to about 50 mmHg, and is selected to be 30 mmHg in this particular embodiment.

In such cases, when the occlusion device positioning test results in a test occlusion phase having a pulsatile pressure 224 of less than 30 mmHg (the minimum threshold value in this embodiment), the control system 140 is configured to output an alert message 171a (FIG. 9A) via the user interface 142 that indicates that a low pulsatile pressure 172a has been detected, and that a repositioning of the occlusion device is recommended. In this situation, the practitioner may activate configurable touch screen button 163 to inform the control system 140 of the practitioner's intent to reposition the occlusion device 122 within the coronary sinus. Then the clinician may proceed to physically reposition the occlusion device 122 and, optionally, restart another occlusion device positioning test. Alternative, the practitioner may activate configurable touch screen button 164 to inform the system 100 of the practitioner's intent to proceed with the PICSO treatment process without repositioning the occlusion device 122. Then the clinician may proceed to physically reposition the occlusion device.

Or, when the occlusion device positioning test results in a monitored pulsatile pressure 224 that is equal to or greater than the example threshold level of 30 mmHg (the minimum threshold value in this embodiment), the control system 140 can provide an alert message 171b (FIG. 9B) that indicates that a sufficient pulsatile pressure 172b has been detected, and that the position of the occlusion device 122 is satisfactory. In this situation, the practitioner may activate configurable touch screen button 164 to continue the treatment process beyond the occlusion device positioning test (without repositioning the occlusion device). While in this example of the occlusion device positioning test the pulsatile pressure was used as the determining pressure value, in other embodiments other pressure-based values or combinations of values can be used to determine whether the occlusion is satisfactory. For example, in some embodiments the global relative pressure 226 (FIG. 8B) drop can be monitored and compared to a predetermined threshold value and used to make a determination as to whether a satisfactory level of occlusion is attained.

Figure 10:
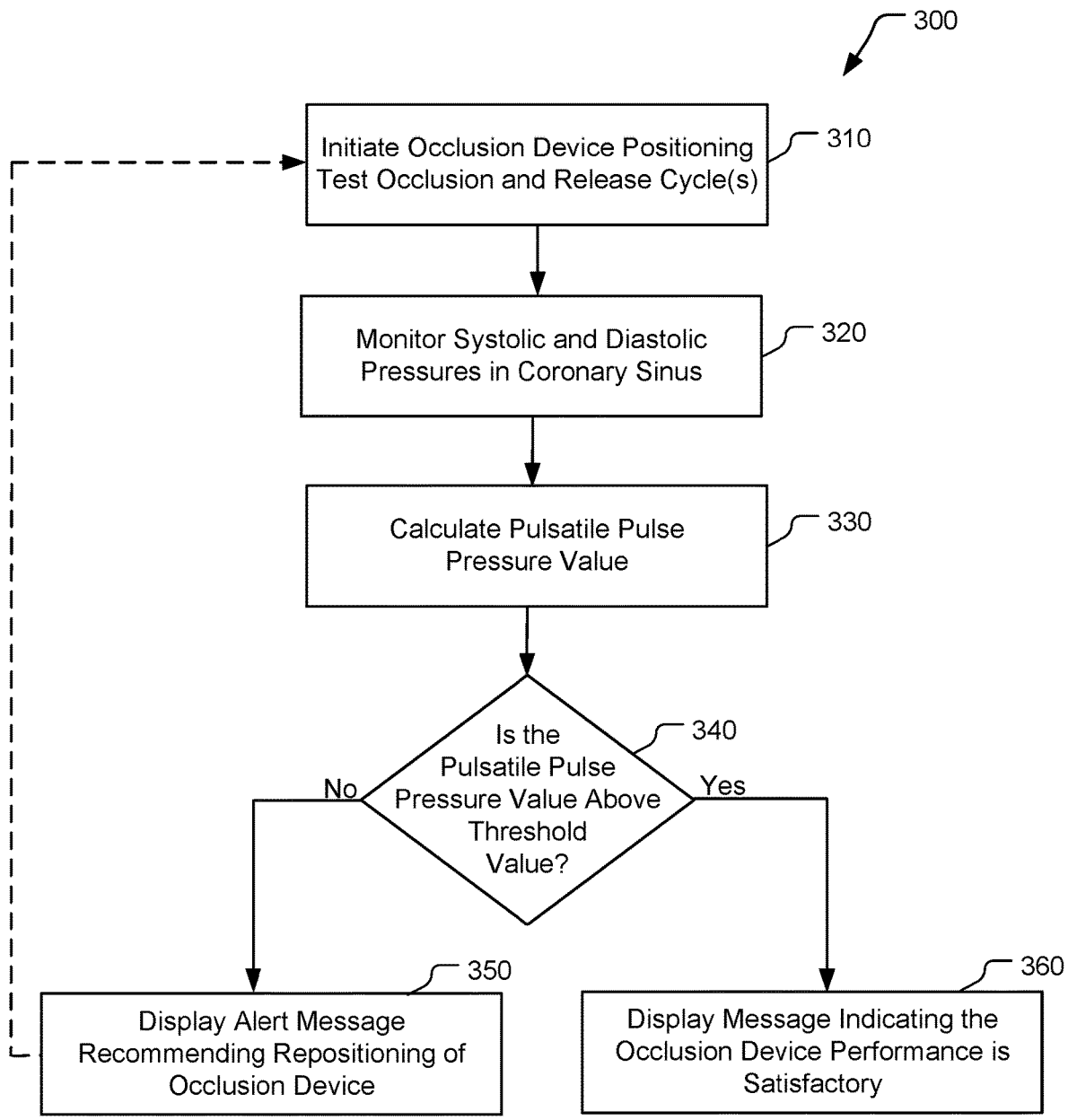
FIG. 10 is a process flow chart for a method of using the system of FIG. 1, in accordance with some embodiments.

Referring to now FIG. 10, some embodiments of the control system 140 can be configured to implement a process 300 for determining whether the occlusion device is located in a satisfactory position within the coronary sinus. In particular implementations, the process 300 illustrated in FIG. 10 can be used to output the alert messages 171a-b as described above in reference to FIGS. 9A and 9B.

At operation 310, the process may include initiating an occlusion device positioning test (preferably after the occlusion device 122 of the catheter 120 is initially placed in the coronary sinus of the patient). Optionally, the occlusion device positioning test can be initiated in response to user input of one or more buttons on the touchscreen interface 142 of the control system 140. The occlusion device positioning test in this embodiment includes the performance of at least one occlusion phase and at least one release phase as automatically controlled by the control system 140. As the occlusion and release cycle(s) are being performed, process 300 continues to operation 320 in which one or more patient characteristics (e.g., pressure-based characteristics in this embodiment, such as the systolic maxima and diastolic minima pressures in the coronary sinus) are detected and stored by the control system 140. The process 300 may continue to operation 330, in which the detected pressure-based characteristics from operation 320 to calculate one or more pressure-based parameters such as the pulsatile pressure (which is calculated in this embodiment from the difference between the systolic plateau pressure and the diastolic plateau pressure during the test occlusion phase). At operation 340, the process 300 compares the calculated pulsatile pressure from operation 330 to a predetermined pulsatile pressure threshold value. As previously described, the threshold value for the pulsatile pressure may be a minimum threshold value selected from a range of 25 mmHg or greater, about 25 mmHg to about 50 mmHg. If the calculated pulsatile pressure is less than the predetermined pulsatile pressure threshold value, the process 300 proceeds to operation 350. At operation 350, the control system 140 displays an alert message on the graphical user interface recommending the repositioning of the occlusion device. In such circumstances, the process 300 can return to operation 310 after the occlusion device is repositioned within the coronary sinus. However, if at operation 340 the calculated pulsatile pressure from operation 330 is greater than or equal to the predetermined pulsatile pressure threshold value, the process 300 proceeds to operation 360. At operation 360, the control system 140 displays a message on the graphical user interface indicating that the occlusion device performance is satisfactory.

Figure 11:
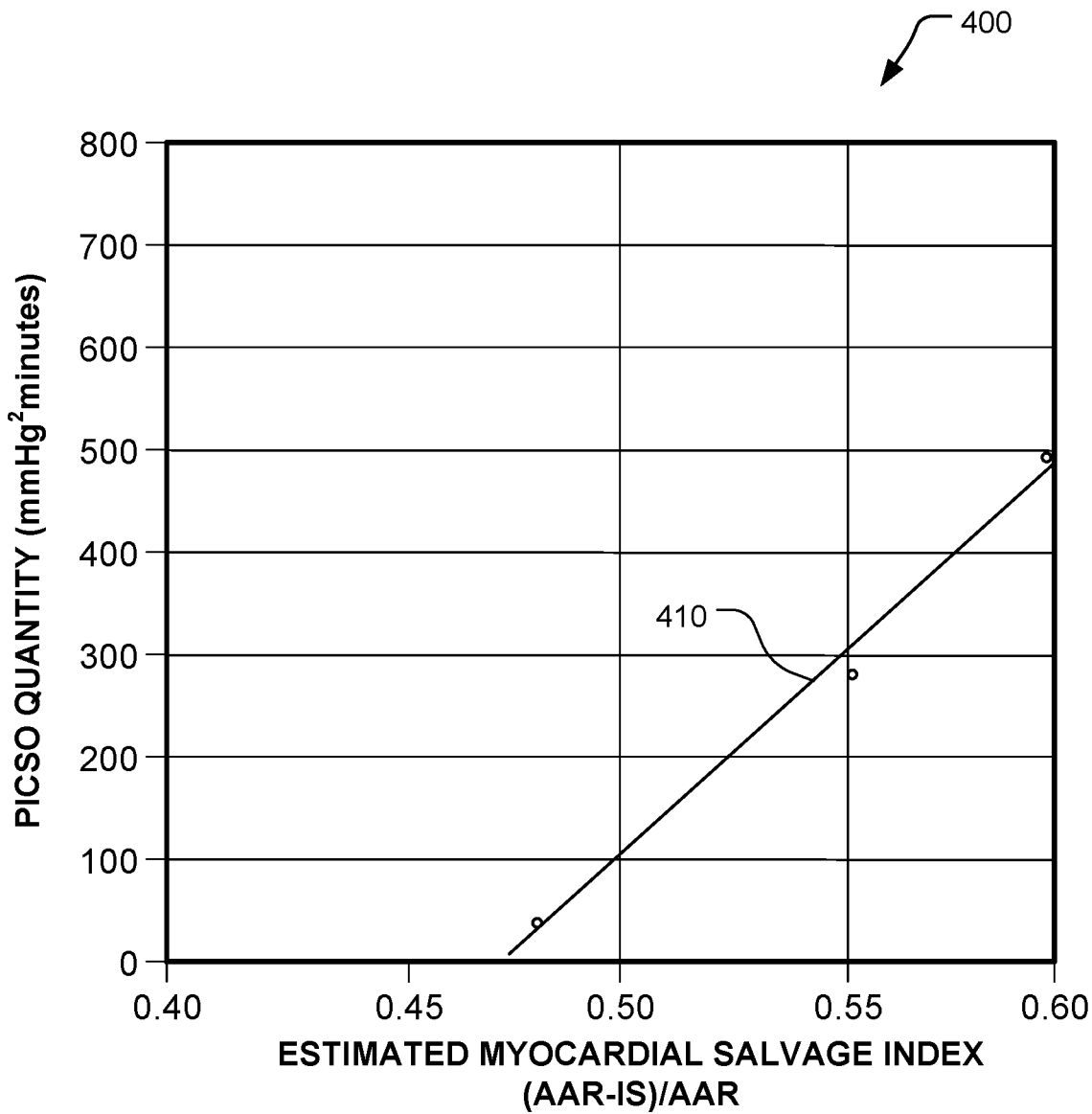
FIG. 11 is a graph of a cumulative dosage value (calculated by the system of FIG. 1) in comparison to an Estimated MSI.

Referring to FIG. 11, in some embodiments of the system described herein, the control system 140 can be configured to not only calculate the cumulative dosage value (e.g., the "PICSO Quantity" or the "PICSO Dose" described above), but the control system 140 can also be configured to estimate an amount of AAR heart tissue that has been salvaged over the course of the successive occlusion phases based at least in part upon the calculated PICSO Quantity value or other cumulative dosage value. For example, the estimated amount of AAR heart tissue that has been salvaged can be characterized according to the previously described Myocardial Salvage Index (MSI), which in some circumstances may have an approximately linear relationship with the PICSO Quantity value calculated by the control system 140. For instances, the control system 140 can store an algorithm that determines the estimated MSI value from the calculated PICSO Quantity value according to a linear model 410, such as one example linear model depicted in FIG. 11. In this example plot, a number of sample data points for various PICSO Quantity values during different PICSO treatment procedures can be plotted, and a linear model 410 is then determined using linear regression or another modeling technique. (In other embodiments, more or different data points beyond the data points shown in FIG. 11 can be used to select the relationship model between the PICSO Quantity and the estimated MSI.) From there, the linear model 410 can be implemented in the form of an algorithm executed by the control system 140 to thereby provide an estimated MSI value based at least in part upon the calculated PICSO Quantity value. It should be understood from the description herein that, in other embodiments, the relationship model between the estimated MSI and the PICSO Quantity value need not be a linear model, but instead may be linear, parabolic, asymptotic, or a combination thereof. In accordance with the teachings herein, the relationship model can be determined from empirical data including multiple different PICSO procedures, and the relationship model can then be implemented in the form of an executable algorithm stored by the control system 140 so as to output the estimated MSI value to the practitioner during use of the system 100.

As shown in FIG. 11, for purposes of correlating the calculated PICSO Quantity (Equation #1 above) to the MSI (Equation #3 below) in this embodiment, the plot in FIG. 11 defines the MSI as the difference of the area at risk (AAR) minus the resulting infarct size, divided by the AAR. Thus, for purposes of determining the relationship model between the calculated PICSO Quantity and the estimated MSI (such as the linear model 410 depicted in FIG. 11), the MSI for each of the empirical data points can be calculated as follows:

$$MSI=(AAR-IS)/AAR, \text{ where:} \quad \text{Equation \#3:}$$

MSI=the myocardial salvage index,
AAR=the myocardial area at risk of infarction, and
IS=infarct size measured at about 3-4 months after treatment.

The AAR is the percentage of the myocardium that is in danger of infarction, as viewed for example by MM (magnetic resonance imaging) during a time period of about less than a week after an acute occlusion of a coronary artery, or other type of cardiac event (e.g., unstable angina, STEMI, NSTEMI, heart failure, and the like). The MSI is a measure of how much of the AAR is salvaged, and is viewed by MM during a time period of about 3-4 months after treatment. For example, if an individual experiences an acute occlusion of a coronary artery and an MRI taken about three days later reveals an AAR of 20%, while a second MRI four months later reveals an IS of 10% of the total myocardium, then the MSI is equal to 0.5 (or 50%). In other words, half of the AAR was salvaged. Similarly, if all of the AAR is salvaged, the MSI would be one (1.0 or 100%). Or, if none of the AAR is salvaged, the MSI would be zero (0.0 or 0%).

Still referring to FIG. 11, the plot 400 illustrates that, in some circumstances, using the system 100 to administer treatment of a particular PICSO Quantity will tend to provide a particular Estimated MSI. In this example, the line 410 of chart 400 indicates that administering a PICSO Quantity of about 100 $mmHg^2$-minutes will tend to provide an Estimated MSI of about 0.5 (or 50%). Also in this example, administering a PICSO Quantity of about 300 $mmHg^2$-minutes will tend to provide an Estimated MSI of about 0.55 (or 55%).

In some embodiments, the relationship model between PICSO Quantity and Estimated MSI can be implemented as part of an algorithm stored and executed by the control system 140 of system 100 such that the control system 140 can contemporaneously calculate the PICSO Quantity and the Estimated MSI based on the operations of the system 100. In particular embodiments, calculated values for PICSO Quantity and Estimated MSI can be displayed on the graphical user interface 142 of the system 100, and these two numeric values can be repeatedly updated with each new occlusion phase in the series of occlusion phases during the PICSO treatment process. A practitioner of the system 100 may use the displayed parameters such as PICSO Quantity and Estimated MSI to enhance the clinician's understanding of the efficacy of the treatment provided by system 100, and to make informed treatment decisions, such as how long to continue the PICSO treatment.

Figure 12:
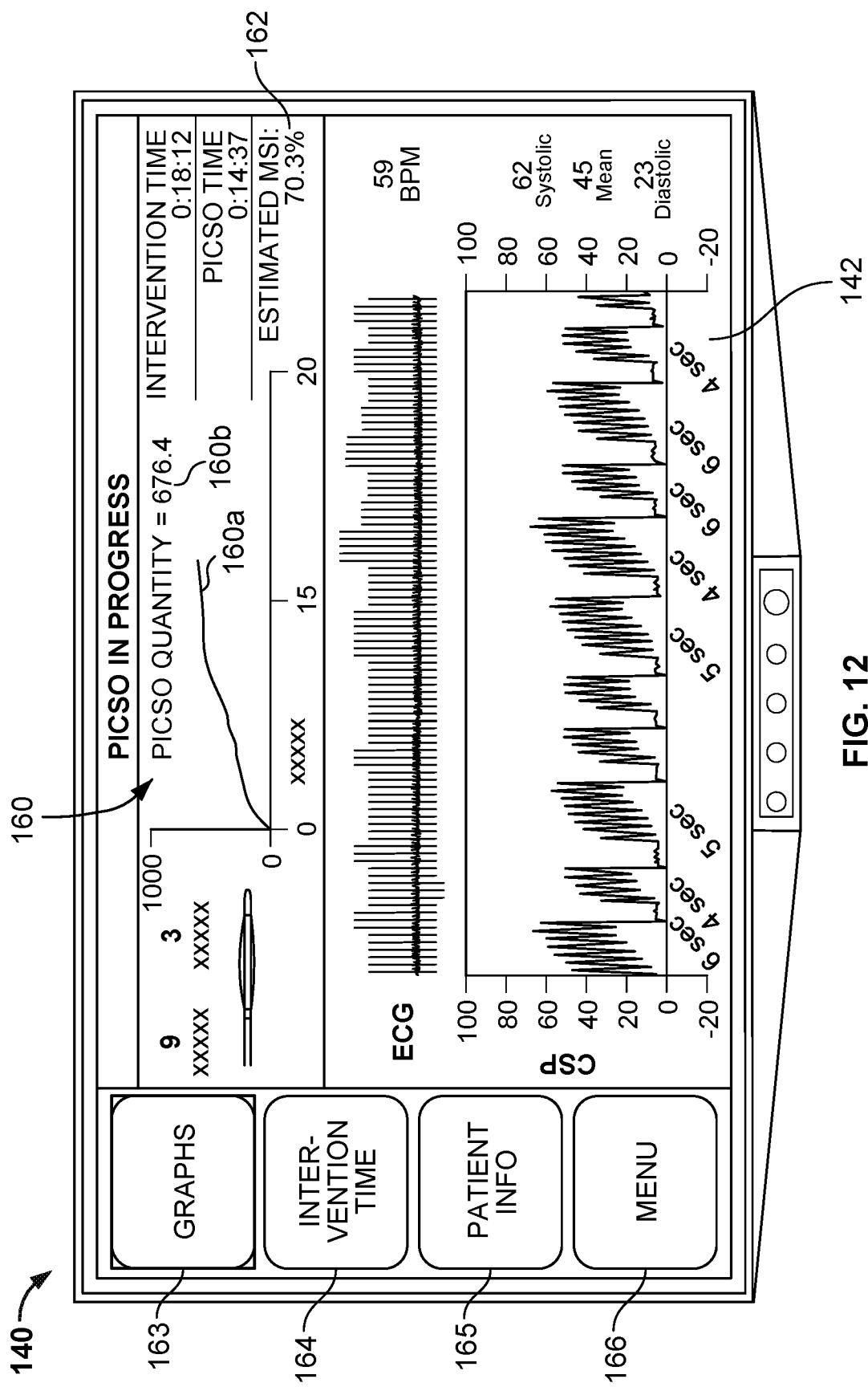
FIG. 12 is a front view of a portion of the control system of FIG. 1, including a graphical user interface of the system of FIG. 1 that outputs updated values of the cumulative dosage value, in accordance with some embodiments.

Referring to now FIG. 12, some embodiments of the control system 140 can include the graphical user interface 142 that outputs one or more cumulative treatment parameters such as PICSO Quantity 160 and Estimated MSI 162. In some circumstances, a practitioner (e.g., an interventional cardiologist in this embodiment) can readily view the updated values of the PICSO Quantity 160 and/or Estimated MSI 162 so as to determine with the PICSO treatment process can be stopped (for example, when the sufficient level(s) of PICSO Quantity 160 and/or Estimated MSI 162 are obtained).

The control system 140 can be configured to calculate the PICSO Quantity 160 and the Estimated MSI 162 using the equations and correlations as described above. For example, the PICSO Quantity 160 parameter can be calculated by the control system 140 using Equation #1 provided above. As previously described, the calculation of PICSO Quantity 160 can be based on characteristics monitored by the control system 140 including (referring to FIG. 8B): (i) systolic plateau pressure 221, (ii) pulsatile pressure 224, (iii) global relative pressure drop 226, and (iv) inflation hold time. The control system 140 in this embodiment is also configured to calculate the Estimated MSI 162 based at least in part upon the PICSO Quantity value or another cumulative dosage value. For example, the control system 140 can calculate the Estimated MSI 162 using the predetermined relationship model between PICSO Quantity 160 and Estimated MSI 162 (such as the relationship model 410 depicted in FIG. 11 or the like).

In this example embodiment of the graphical user interface 142, the PICSO Quantity 160 is displayed both graphically 160a and numerically 160b, whereas the Estimated MSI 162 is displayed only numerically. In alternative embodiments, the Estimated MSI 162 may also be displayed graphically. Additionally, a predetermined targeted level (as input by the practitioner or otherwise pre-stored by the control system 140), or a message indicating the attainment of the predetermined targeted level, of PICSO Quantity 160 and/or Estimated MSI 162 may be displayed in some embodiments.

Figure 13:
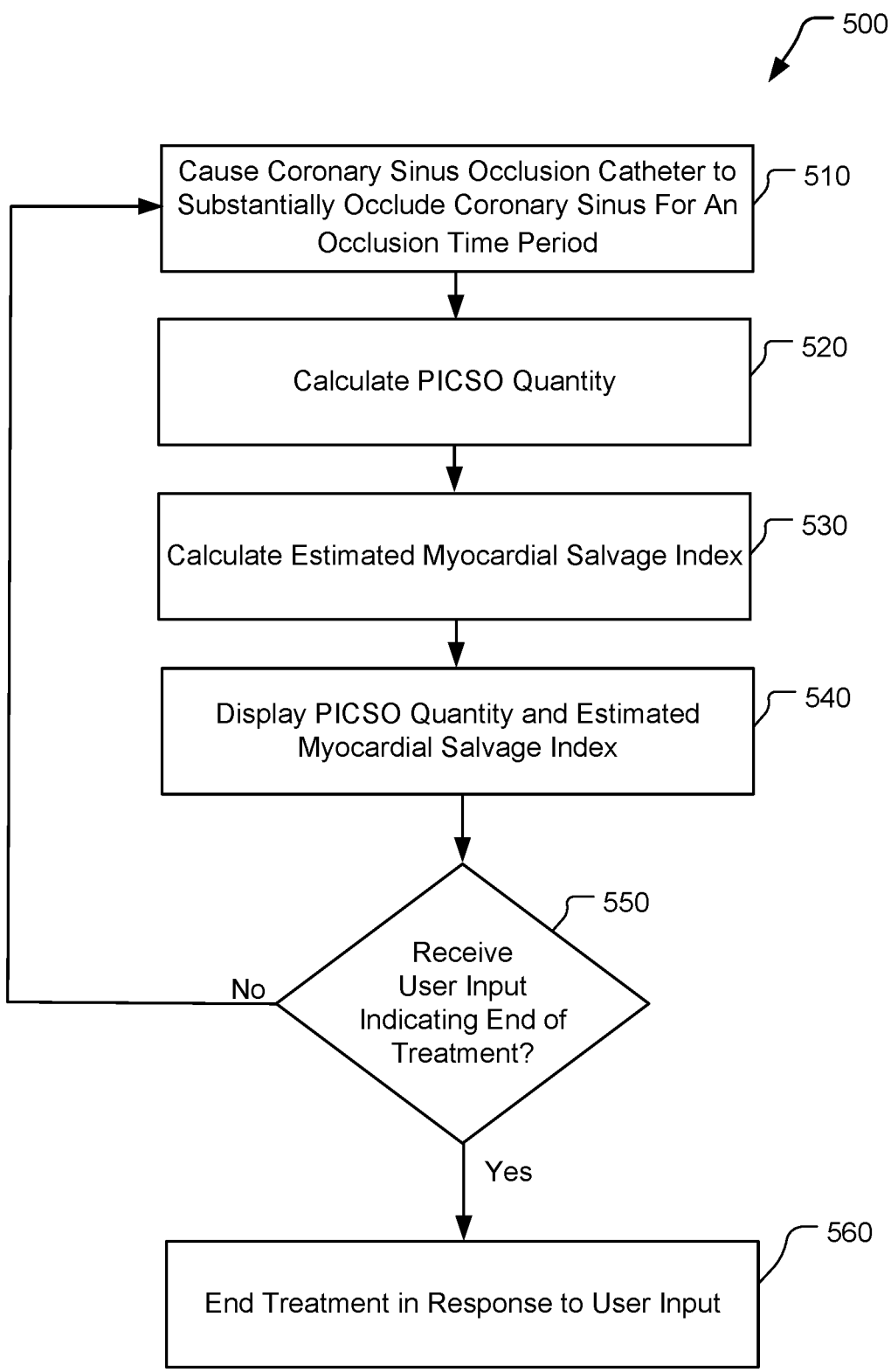
FIG. 13 is a process flow chart for a method of using the system of FIG. 1, in accordance with particular embodiments.

Referring now to FIG. 13, some embodiments of a treatment monitoring process 500 can be implemented by the control system 140 to calculate and output the cumulative dosage value (e.g., the PICSO Quantity in this embodiment), the Estimated MSI, or both. The treatment monitoring process 500 can be implemented, for example, to output via the user interface 142 (and to repeatedly update) the PICSO Quantity and Estimated MSI as illustrated FIGS. 11 and 12.

The process may include operation 510, in which the control system 140 controls the coronary sinus occlusion catheter to substantially occlude the coronary sinus for an occlusion time period (e.g., an occlusion phase). As described above, during the occlusion phases (and the release phases) of the treatment, the control system 140 can monitor pressure-based characteristics in the coronary sinus such as the systolic pressure maxima and diastolic pressure minima. The control system 140 can be configured to perform a curve fitting operation so as to determine a curve fit line for the systolic pressure maxima and diastolic pressure minima occurring over a series of consecutive heartbeats during the occlusion phase. These curve fit lines define plateau values of the systolic maxima and diastolic minima. The control system 140 can calculate a pulsatile pressure (e.g., item 224 in FIG. 8B) which is the difference between the systolic maxima plateau and the diastolic minima plateau. The control system 140 can also be configured to calculate an average of the systolic and diastolic pressures during the release phase, which is the deflation average pressure (e.g., item 223 in FIG. 8B). Further, the control system 140 can calculate the global relative pressure drop (e.g., item 226 in FIG. 8B), which is the difference between the systolic maxima plateau and the average of the systolic and diastolic pressures of the release phase.

The process 500 can also include operation 520, in which the control system 140 calculates the PICSO Quantity parameter or another cumulative dosage value (as described above). In this embodiment, the PICSO Quantity parameter can be calculated by the control system 140 using Equation #1 above. As described below, an updated PICSO Quantity can be calculated by the control system 140 at least after the completion of each occlusion and release cycle. As previously described, the PICSO Quantity value is a cumulative dosage value, and therefore accounts for the cumulative effects of the successive cycles of occlusion phases and release phases during the course of the PICSO treatment (as described by Equation #1).

The process 500 can also include operation 530, in which the control system 140 calculates the Estimated MSI parameter. The Estimated MSI parameter can be calculated by the control system 140 based at least in part upon the PICSO Quantity value or another cumulative dosage value. For example, the control system 140 can calculate the Estimated MSI 162 using the predetermined relationship model between PICSO Quantity 160 and Estimated MSI 162 (such as the relationship model 410 depicted in FIG. 11 or the like). As described in more detail below, an updated Estimated MSI parameter can be calculated by the control system 140 at least after the completion of each occlusion and release cycle (e.g., each time the PICSO Quantity value is updated).

The process 500 can also include operation 540, in which the control system 140 outputs on the graphical user interface 142 the current values for PICSO Quantity and Estimated MSI. The display of the PICSO Quantity and Estimated MSI values can be updated at least after each occlusion and release cycle, or more often in some cases. For example, as shown in FIG. 12, the PICSO Quantity is displayed as 676.4 mmHg$^2$-minutes, and the Estimated MSI is displayed as 70.3%. By providing a display of the current PICSO Quantity and Estimated MSI, the control system 140 provides the practitioner with meaningful, time-sensitive information indicative of the progress of the PICSO treatment being administered by the system 100. In some situations, the practitioner can make a decision as to whether to cease or continue administering treatment based at least in part on the PICSO Quantity displayed by the user interface 142, the Estimated MSI displayed by the user interface 142, or both. For example, the practitioner may compare the Estimated MSI to a predetermined target value to evaluate whether to end or continue the treatment.

The process 500 may also include operation 550, in which the control system 140 receives user input indicating an end to the treatment using the system 100. For example, if the practitioner reviews the PICSO Quantity displayed by the user interface 142, the Estimated MSI displayed by the user interface 142, or both, and then decides that sufficient progress was achieved during the PICSO treatment or that the PICSO treatment should end for other reasons, the practitioner can press one or more buttons on the touchscreen interface 142 of the control system 140 to indicate that the treatment process should end. In such circumstances, the process 500 continues to operation 560, in which the control system 140 ceases the intermittent occlusion phases of the coronary sinus in response to the user input received at operation 550. From there, the coronary sinus occlusion catheter 120 is deactivated and prepared for withdrawal from the patient's heart.

If no such user input (at operation 550) is received by the control system 140 (e.g., no user input is received within a selected time period), the process 500 can return to operation 510 in which a new occlusion and release cycle is initiated. As such, the process 500 can repeatedly cycle so as to provide a newly updated PICSO Quantity value (or other cumulative dosage value) and a newly updated estimated MSI value for each new occlusion and release cycle.

A number of embodiments of the invention have been described. Nevertheless, it will be understood that various modifications may be made without departing from the scope of the invention. Accordingly, other embodiments are within the scope of the following claims.

What is claimed is:

1. A method, comprising:
   receiving a pressure sensor data signal indicative of a coronary sinus pressure after a occlusion catheter has substantially occluding the coronary sinus during an occlusion phase in a sequence of multiple occlusion phases;
   storing data in a computer-readable memory device of a control console indicative of at least pressure maxima and pressure minima measured during the sequence of multiple occlusion phases;
   after each occlusion phase in the sequence of multiple occlusion phases, calculating a cumulative dosage value indicative of a measurement of progress of reducing an infarct size, the cumulative dosage value being calculated based at least in part upon the data the pressure maxima and pressure minima measured during the sequence of multiple occlusion phases; and
   after each occlusion phase in the sequence of multiple occlusion phases, updating a display of: the calculated cumulative dosage value presented on a display device of the control console, an estimated amount of salvaged heart muscle tissue based upon the calculated cumulative dosage value, or both.

2. The method of claim 1, wherein said calculating includes calculating the cumulative dosage value in units of $(Pressure)^2 \times (time)$.

3. The method of claim 1, after each occlusion phase in the sequence of multiple occlusion phases, calculating the estimated amount of salvaged heart muscle tissue based at least in part upon a predetermined mathematical relationship between the estimated amount of salvaged heart muscle tissue and the calculated cumulative dosage value.

4. The method of claim 3, wherein the estimated amount of salvaged heart muscle tissue based at least in part upon a linear relationship between the estimated amount of salvaged heart muscle tissue and the calculated cumulative dosage value.

5. The method of claim 1, wherein said updating the display comprises contemporaneously displaying on the display device both the calculated cumulative dosage value and the estimated amount of salvaged heart muscle tissue.

6. The method of claim 1, further comprising calculating the cumulative dosage value to provide a numerical value indicative of cumulative effects of redistributing blood flow over two or more successive occlusion phases.

7. The method of claim 1, further comprising further outputting an output signal encoding the calculated cumulative dosage value, the estimated amount of salvaged heart muscle tissue, or both.

8. The method of claim 1, wherein the estimated amount of salvaged heart muscle tissue is an estimated myocardial salvage index based upon a linear relationship model with the calculated cumulative dosage value.

9. The method of claim 1, further comprising updating the calculated cumulative dosage value, the estimated amount of salvaged heart muscle tissue, or both after each cycle of one occlusion phase and one release phase.

10. The method of claim 1, wherein said updating the display comprises contemporaneously displaying the calculated cumulative dosage value and the estimated amount of salvaged heart muscle tissue on a touchscreen user interface.

11. A method, comprising:
    receiving a pressure sensor data signal indicative of a coronary sinus pressure after a occlusion catheter has substantially occluding the coronary sinus during an occlusion phase of an occlusion device positioning test;
    storing data in a computer-readable memory device of an occlusion device control system indicative of at least pressure maxima and pressure minima measured during the sequence of multiple occlusion phases;
    after the occlusion phase of the occlusion device positioning test, calculating a pulsatile pressure parameter, the pulsatile pressure parameter being calculated based at least in part upon the data the pressure maxima and pressure minima measured during the occlusion phase of the occlusion device positioning test; and
    in response to detecting that the pulsatile pressure parameter is less than a minimum threshold value, outputting an alert via a user interface of the control system indicating a recommendation to reposition of the occlusion catheter in the coronary sinus.

12. The method of claim 11, further comprising in response to detecting that the pulsatile pressure parameter is greater than or equal to the minimum threshold value, outputting a message via the user interface of the control system confirming the position of the occlusion catheter in the coronary sinus is satisfactory.

13. The method of claim 11, further comprising:
    after outputting the message confirming the position of the occlusion catheter in the coronary sinus, controlling the occlusion catheter to intermittently occlude the coronary sinus during a sequence of multiple occlusion phases;
    after each occlusion phase in the sequence of multiple occlusion phases, calculating a cumulative dosage value indicative of a measurement of progress of reducing an infarct size; and
    after calculating the cumulative dosage value, updating the user interface of the control system to show updated values for: the calculated cumulative dosage value, an estimated amount of salvaged heart muscle tissue based upon the calculated cumulative dosage value, or both.

14. The method of claim 11, wherein said calculating occurs via the occlusion device control system.

15. The method of claim 11, further comprising monitoring the pulsatile pressure parameter for each occlusion phase/release phase cycle.

16. The method of claim 11, wherein the minimum threshold value for the pulsatile pressure is a numeric value selected from a range of 25 mmHg or greater.

17. The method of claim 16, wherein the minimum threshold value for the pulsatile pressure is a numeric value selected from a range of about 25 mmHg to about 50 mmHg.

18. The method of claim 17, wherein the minimum threshold value for the pulsatile pressure is a numeric value of about 30 mmHg.

19. The method of claim 11, further comprising, in response to detecting that the pulsatile pressure parameter is equal to or greater than the minimum threshold value, providing an alert message that indicates that a sufficient pulsatile pressure has been detected and that the position of the occlusion device is satisfactory.

20. A computer readable-medium storing instructions thereon which when executed cause a processor to carry out the operations of method 11.

\* \* \* \* \*

UNITED STATES PATENT AND TRADEMARK OFFICE
CERTIFICATE OF CORRECTION

PATENT NO. : 10,561,425 B2
APPLICATION NO. : 15/858856
DATED : February 18, 2020
INVENTOR(S) : Lars Roman Schiemanck and Martin Haidacher It is certified that error appears in the above-identified patent and that said Letters Patent is hereby corrected as shown below:

In the Claims

Column 27, Line 5, in Claim 20, delete "method 11." and insert -- method of claim 11. --, therefor.

Signed and Sealed this
Ninth Day of June, 2020

Andrei Iancu
*Director of the United States Patent and Trademark Office*